US009457041B2

(12) United States Patent
Kulkarni et al.

(10) Patent No.: US 9,457,041 B2
(45) Date of Patent: Oct. 4, 2016

(54) CONTROLLED RELEASE NANOPARTICLES AND METHODS OF USE

(71) Applicants: Prajakta S. Kulkarni, Fargo, ND (US); Manas K. Haldar, Fargo, ND (US); Sanku Mallik, West Fargo, ND (US); D. K. Srivastava, Reilies Acres, ND (US)

(72) Inventors: Prajakta S. Kulkarni, Fargo, ND (US); Manas K. Haldar, Fargo, ND (US); Sanku Mallik, West Fargo, ND (US); D. K. Srivastava, Reilies Acres, ND (US)

(73) Assignee: NDSU Research Foundation, Fargo, ND (US)

( * ) Notice: Subject to any disclaimer, the term of this patent is extended or adjusted under 35 U.S.C. 154(b) by 0 days.

(21) Appl. No.: 14/744,705

(22) Filed: Jun. 19, 2015

(65) Prior Publication Data

US 2016/0000724 A1 Jan. 7, 2016

Related U.S. Application Data

(60) Provisional application No. 62/015,213, filed on Jun. 20, 2014.

(51) Int. Cl.
| | |
|---|---|
| *A61K 9/14* | (2006.01) |
| *A61K 31/7068* | (2006.01) |
| *A61K 49/00* | (2006.01) |
| *A61K 9/00* | (2006.01) |
| *A61K 9/127* | (2006.01) |

(52) U.S. Cl.
CPC ......... *A61K 31/7068* (2013.01); *A61K 9/0019* (2013.01); *A61K 9/1271* (2013.01); *A61K 49/0093* (2013.01)

(58) Field of Classification Search
CPC .................................................. A61K 31/7068
See application file for complete search history.

(56) References Cited

U.S. PATENT DOCUMENTS

| | | | |
|---|---|---|---|
| 5,171,578 A | 12/1992 | Bally et al. | |
| 5,204,096 A | 4/1993 | Neurath et al. | |
| 5,258,499 A | 11/1993 | Konigsberg et al. | |
| 7,108,863 B2 | 9/2006 | Zalipsky et al. | |
| 2006/0210549 A1 | 9/2006 | Srivastava et al. | |
| 2006/0240009 A1 | 10/2006 | Zalipsky et al. | |

FOREIGN PATENT DOCUMENTS

| | | |
|---|---|---|
| CN | 1509166 A | 6/2004 |
| CN | 102600080 A | 9/2013 |
| WO | WO 01/00247 A1 | 1/2001 |
| WO | WO 02/076248 A1 | 10/2002 |

OTHER PUBLICATIONS

Abbott, "Cell culture: biology's new dimension," *Nature*, Aug. 2003; 424(6951):870-872.
Akers et al., "Detection of MMP-2 and MMP-9 activity in vivo with a triple-helical peptide optical probe," *Bioconjugate Chemistry*, Mar. 2012; 23(3):656-663. Available online Feb. 29, 2012.
Babincová et al., "Laser triggered drug release from magnetoliposomes," *Journal of Magnetism and Magnetic Materials*, 1999; 194(1-3):163-166.
Banerjee et al., "Release of Liposomal Contents by Cell-Secreted Matrix Metalloproteinase-9," *Bioconjugate Chemistry*, 2009; 20(7):1332-1339.
Banerjee, "Liposomes: Applications in Medicine," *J. Biomaterials Applications*, 2001; 16:3-21.
Banerjee et al, "Microwave-assisted synthesis of triple-helical, collagen-mimetic lipopeptides," *Nature protocols*, Jan. 2010; 5(1):39-50.
Banerjee et.al,"Liposome-mediated amplified detection of cell-secreted matrix metalloproteinase-9," *Chem. Communications*, May 2010; 46:3209-3211.
Bennett et al., "Photoactivated Enhancement of Liposome Fusion," *Biochemistry*, Mar. 1995; 34(9):3102-3113.
Bondurant et al., "Photoinduced Destabilization of Sterically Stabilized Liposomes," *Journal of the American Chemical Society*, 1998; 120(51):13541-13542.
Boomer et al., "Acid-Triggered Release from Sterically Stabilized Fusogenic Liposomes via a Hydrolytic DePEGylation Strategy," *Langmuir*, 2003; 19:6408-6415.
Brusa et al., "Antitumor activity and pharmacokinetics of liposomes containing lipophilic gemcitabine prodrugs," *Anticancer Res.*, 2007; 27:195-199.
Cai et al., "Effective Gene Delivery Using Stimulus-Responsive Catiomer Designed with Redox-Sensitive Disulfide and Acid-Labile Imine Linkers," *Biomacromolecules*, 2012; 13(4):1024-1034.
Celano et al., "Cytotoxic effects of gemcitabine-loaded liposomes in human anaplastic thyroid carcinoma cells," *BMC Cancer*, 2004; 4(1):63.
Chandaroy et al., "Temperature-controlled content release from liposomes encapsulating Pluronic F127," *Journal of Controlled Release*, Sep. 2001; 76(1-2):27-37.
Chandrasekaran et al., "Gather Round: In Vitro Tumor Spheroids as Improved Models of In Vivo Tumors," *Journal of Bioengineering & Biomedical Science*, 2012; 2:4.

(Continued)

*Primary Examiner* — Paul Dickinson
(74) *Attorney, Agent, or Firm* — Mueting, Raasch & Gebhardt, P.A.

(57) ABSTRACT

Provided herein are nanoparticles that include a lipid layer and a compartment surrounded by the lipid layer. The lipid layer may include a lipid and a lipoprotein. The lipid may include a POPE lipid covalently attached to a hydrophilic polymer by a disulfide bond. The lipoprotein may include a trigger protein. The concentration of the first lipid may be between 1 mol % and 30 mol %. The disulfide bond of the first lipid is stable under conditions that include 10% human serum and is broken under conditions that include 50 micromolar glutathione. The hydrophilic polymer may include a PEG molecule. The trigger protein may include an amino acid repeat region, such as (GPX)n. The trigger protein may include a peptide bond that is cleaved by a gelatinase (e.g., gelatinase-B protease), or a member of the ADAM family of proteases (e.g., ADAM10 protease). Also provided are methods of using the nanoparticles.

19 Claims, 15 Drawing Sheets

(56) References Cited

OTHER PUBLICATIONS

Chen et al., "Disruptions of occludin and claudin-5 in brain endothelial cells in vitro and in brains of mice with acute liver failure," *Hepatology*, 2009; 50(6):1914-1923.
Choi et al., "A cellular Trojan Horse for delivery of therapeutic nanoparticles into tumors," *Nano Lett.*, 2007; 7(12):3759-3765.
Coleman et al., "Role of Peroxisome Proliferator-Activated Receptor W8 and B-Cell Lymphoma-6 in Regulation of genes involved in metastasis and migration in pancreatic cancer cells," *PPAR Res*, 2013; 2013:121956.
Cosco et al., "In vivo activity of gemcitabine-loaded PEGylated small unilamellar liposomes against pancreatic cancer," *Cancer Chemother. Pharmacol.*, 2009; 64(5):1009-1020.
Dalberg et al., "Gelatinase A, Membrane Type 1 Matrix Metalloproteinase, and Extracellular Matrix Metalloproteinase Inducer mRNA Expression: Correlation with Invasive Growth of Breast Cancer," *World Journal of Surgery*, Mar. 2000; 24(3):334-340.
Davidsen et al., "Drug delivery by phospholipase $A_2$ degradable liposomes," *International Journal of Pharmaceutics*, 2001; 214(1-2):67-69.
Davidsen et al., "Secreted phospholipase A2 as a new enzymatic trigger mechanism for localised liposomal drug release and absorption in diseased tissue," *Biochimica et Biophysica Acta*, 2003; 1609:95-101.
Davis et al., "Cholesterol Phosphate Derivatives: Synthesis and Incorporation into a Phosphatase and Calcium-Sensitive Triggered Release Liposome," *Bioconjugate Chemistry*, 1998; 9(6):783-792.
de la Rica et al., "Enzyme-responsive nanoparticles for drug release and diagnostics," *Advanced Drug Delivery Reviews*, Aug. 2012; 64(11):967-978.
de Lima et al., "Cationic Liposomes for Gene Delivery: From Biophysics to Biological Applications," *Current Medicinal Chemistry*, 2003; 10(14):1221-1231.
Drummond et al., "Current status of pH-sensitive liposomes in drug delivery," *Progress in Lipid Research*, Sep. 2000; 39(5):409-460.
Duncan, "The dawning era of polymer therapeutics," *Nature Reviews Drug Discovery*, May 2003; 2(5):347-360.
Dvorak et al., "Identification and Characterization of the Blood Vessels of Solid Tumors That Are Leaky to Circulating Macromolecules," *Am. J. Pathol.*, Oct. 1988; 133(1):95-109.
Elegbede et al., "Mechanistic Studies of the Triggered Release of Liposomal Contents by Matrix Metalloproteinase-9," *J. Am. Chem. Soc.*, Aug. 2008; 130(32):10633-10642.
Estrela et al., "Glutathione in Cancer Biology and Therapy," *Critical Reviews in Clinical Laboratory Sciences*, 2006; 43(2): 143-181.
Fan et al., "Backbone dynamics of (Pro-Hyp-Gly)10 and a designed collagen-like triple-helical peptide by 15N NMR relaxation and hydrogen-exchange measurements," *Biochemistry*, Dec. 1993; 32(48):13299-13309.
Felnerova et al., "Liposomes and virosomes as delivery systems for antigens, nucleic acids and drugs," *Current Opinion in Biotechnology*, Dec. 2004; 15(6):518-529.
Fields et al., "Solid-Phase synthesis and stability of triple-helical peptides incorporating native collagen sequences," *Biopolymers*, Nov. 1993; 33(11):1695-1707.
Fisher et al., "Phototherapy for scleroderma: biologic rationale, results, and promise," *Current Opinion in Rheumatology*, Nov. 2002; 14(6):723-726.
Fleige et al., "Stimuli-responsive polymeric nanocarriers for the controlled transport of active compounds: Concepts and applications," *Advanced Drug Delivery Reviews*, Jun. 2012; 64(9):866-884.
Francis et al., "In Vitro Evaluation of pH-Sensitive Polymer/Niosome Complexes," *Biomacromolecules*, 2001; 2(3):741-749.
Fuertges et al., "The clinical efficacy of poly(ethylene glycol)-modified proteins," *Journal of Controlled Release*, Jan. 1990; 11(1-3):139-148.
Gabizon et al., "Liposomal anthracyclines—from basics to clinical approval of pegylated liposomal doxorubicin," In *Liposomes: Rational Design*; Janoff, A. S. (Ed.), Marcel Dekker, New York, 1999, pp. 343-362.
Gabizon et al., "Tumor cell targeting of liposome-entrapped drugs with phospholipid-anchored folic acid—PEG conjugates," *Advanced Drug Delivery Reviews*, Apr. 2004; 56(8):1177-1192.
Ganta et al., "A review of stimuli-responsive nanocarriers for drug and gene delivery," *Journal of Controlled Release*, Mar. 2008; 126(3):187-204.
Gao et al., "PEG with Observable Shedding," *Angew Chem Int Ed Engl.*, Sep. 2010; 49(37): 6567-6571.
Genbank Accession No. BC002576: National Center for Biotechnology Information, National Library of Medicine, National Institutes of Health, GenBank Locus: BC002576 3065 by mRNA linear PRI Jul. 15, 2006, "*Homo sapiens* matrix metallopeptidase 2 (gelatinase A, 72kDa gelatinase, 72kDa type IV collagenase), mRNA (cDNA clone MGC:2313 Image:3161383), complete cds," [online]. Bethesda, MD [retrieved on Feb. 23, 2016]. Retrieved from the Internet: <URL: http://www.ncbi.nlm.nih.gov/nuccore/BC002576>; 4 pgs.
Genbank Accession No. BC006093: National Center for Biotechnology Information, National Library of Medicine, National Institutes of Health, GenBank Locus: BC006093 2373 by mRNA linear PRI Jul. 15, 2006, "*Homo sapiens* matrix metallopeptidase 9 (gelatinase B, 92kDa gelatinase, 92kDa type IV collagenase), mRNA (cDNA clone MGC:12688 Image:4054882), complete cds," [online]. Bethesda, MD [retrieved on Feb. 23, 2016]. Retrieved from the Internet: <URL: http://www.ncbi.nlm.nih.gov/nuccore/BC006093>; 3 pgs.
Gerasimov et al., "Cytosolic drug delivery using pH- and light-sensitive liposomes," *Advanced Drug Delivery Reviews*, Aug. 1999; 38:317-338.
Goodman et al., "Collagen mimetics," *Biopolymers (Peptide Science)*, 1998; 47:127-142.
Grab et al., "Promotion of Fibroblast Adhesion by Triple-helical Peptide Models of Type I Collagen-derived Sequences," *The Journal of Biological Chemistry*, May 1996; 271(21):12234-12240.
Gress et al., "Expression and in-situ localization of genes coding for extracellular matrix proteins and extracellular matrix degrading proteases in pancreatic cancer," *International Journal of Cancer*, Aug. 1995; 62(4):407-413.
Han et al., "Stimuli-Triggered Growth and Removal of a Bioreducible Nanoshell on Nanoparticles," *Macromolecular Rapid Communications*, Mar. 2014; 35(6):649-654.
Hanemaaijer et al., "Increased gelatinase-A and gelatinase-B activities in malignant vs. benign breast tumors," *International Journal of Cancer*, Apr. 2000; 86(2):204-207.
Hayashi et al., "Temperature Sensitization of Liposomes Using Copolymers of N-Isopropylacrylamide," *Bioconjugate Chemistry*, 1999; 10(3):412-418.
Heidemann et al., "Synthesis and investigation of collagen model peptides," *Advances in Polymer Science*, 1982; 43:143-203.
Hsieh et al., "Expression of matrix metalloproteinase-9 (gelatinase B) in gouty arthritis and stimulation of MMP-9 by urate crystals in macrophages," *Journal of Cellular Biochemistry*, Jul. 2003; 89(4):791-799.
Hu et al., "Trypsin induced destabilization of liposomes composed of dioleoylphosphatidylethanolamine and glycophorin," *Biochemical and Biophysical Research Communications*, 1986; 141(3):973-978.
Ishida et al., "Liposome Clearance," *Biosciences Reports*, 2002; 22:197-224.
Jefferson et al., "Incorporation of Achiral Peptoid-Based Trimeric Sequences into Collagen Mimetics," *Journal of the American Chemical Society*, Aug. 1998; 120(30):7420-7428.
Jiang et al., "Effect of gemcitabine on the expression of apoptosis-related genes in human pancreatic cancer cells," *World Journal of Gastroenterology*, 2006; 12(10):1597-1602.
Kähäri et al., "Matrix metalloproteinases in skin," *Experimental Dermatology*, Oct. 1997; 6(5)199-213.
Karoonuthaisiri et al., "Destabilization of fatty acid-containing liposomes by polyamidoamine dendrimers," *Colloids and Surfaces B: Biointerfaces*, Mar. 2003, 27(4):365-375.

(56) References Cited

OTHER PUBLICATIONS

Kee et al., "The Relationship Between Gelatinase A Activity in Aqueous Humor and Glaucoma," *Journal of Glaucoma*, Feb. 1999; 8(1):51-55.

Kerkela et al., "Matrix metalloproteinases in tumor progression: focus on basal and squamous cell skin cancer," *Experimental Dermatology*, Apr. 2003; 12(2):109-125.

Kiyama et al., "Homology Modeling of Gelatinase Catalytic Domains and Docking Simulations of Novel Sulfonamide Inhibitors," *Journal of Medicinal Chemistry*, May 1999; 42(10):1723-1738.

Knapinska et al., "Chemical Biology for Understanding Matrix Metalloproteinase Function," *ChemBioChem*, Sep. 2012; 13(14):2002-2020.

Koning et al., "Efficient intracellular delivery of 5-fluorodeoxyuridine into colon cancer cells by targeted immunoliposomes," *Cancer Detection Prevention*, Oct. 2002; 26(4):299-307.

Koo et al., "Disulfide-cross-linked PEG-poly(amino acid)s copolymer micelles for glutathione-mediated intracellular drug delivery," *Chemical Communications*, Dec. 2008; 48:6570-6572.

Koshiba et al., "Detection of matrix metalloproteinase activity in human pancreatic cancer," *Surgery Today*, 1997; 27(4):302-304.

Kossakowska et al., "Elevated Plasma Gelatinase A (MMP-2) Activity Is Associated with Quiescent Crohn's Disease," *Annals of the New York Academy of Sciences*, Jun. 1999; 878:578-580.

Kramer et al., "Staggered molecular packing in crystals of a collagen-like peptide with a single charged pair," *Journal of Molecular Biology*, Sep. 2000; 301(5):1191-1205.

Kramer et al., "The crystal and molecular structure of a collagen-like peptide with a biologically relevant sequence," *Journal of Molecular Biology*, Aug. 2001; 311(1):131-147.

Kulkarni, "MMP-9 responsive liposomes for targeted delivery to pancreatic cancer cells," slides presented at North Dakota State University on Mar. 14, 2014. 44 pages.

Kulkarni et al., "MMP-9 Responsive PEG Cleavable Nanovesicles for Efficient Delivery of Chemotherapeutics to Pancreatic Cancer," *Molecular Pharmaceutics*, Jul. 2014; 11(7):2390-2399.

Kumar et al., "Cationic Transfection Lipids in Gene Therapy: Successes, Set-backs, Challenges and Promises," *Current Medicinal Chemistry*, Jul. 2003; 10(14):1297-1306.

Kwak et al., "TREN (Tris(2-aminoethyl)amine): An Effective Scaffold for the Assembly of Triple Helical Collagen Mimetic Structures," *Journal of the American Chemical Society* Nov. 2002; 124(47):14085-14091.

Lasic, "Novel applications of liposomes," *Trends in Biotechnology*, Jul. 1998; 16(7):307-321.

Leamon et al., "Folate-targeted chemotherapy," *Advanced Drug Delivery Reviews*, Apr. 2004; 56(8):1127-1141.

Lee et al., "Polymersomes for drug delivery: Design, formation and characterization," *Journal of Controlled Release*, Jul. 2012; 161(2):473-483.

Li et al., "Functional polymorphism of liposomal gene delivery vectors: lipoplex and lipopolyplex," In *Liposomes: Rational Design*; Janoff, A. S. (Ed.), Marcel Dekker, New York, 1999, pp. 89-124.

Li et al., "Dithiane-Based Photolabile Amphiphiles: Toward Photolabile Liposomes," *Langmuir*, 2003; 19(16):6381-6391.

Li et al., "Stealth Nanoparticles: High Density but Sheddable PEG is a Key for Tumor Targeting," *Journal of Controlled Release*, Aug. 2010; 145(3):178-181.

Li et al., "PEG-sheddable polyplex micelles as smart gene carriers based on MMP-cleavable peptide-linked block copolymers," *Chemical Communications*, Aug. 2013; 49(62):6974-6976.

Liotta et al., "Metastatic potential correlates with enzymatic degradation of basement membrane collagen," *Nature*, Mar. 1980; 284(5751):67-68.

Liu, "Reduction- and thermo-sensitive star polypeptide micelles and hydrogels for on-demand drug delivery," *Chemical Communications*, 2013; 49(12):1229-1231.

Longati et al., "3D pancreatic carcinoma spheroids induce a matrix-rich, chemoresistant phenotype offering a better model for drug testing," *BMC Cancer*, 2013; 13(1):1-13.

Määttä et al., "Differential Expression of Matrix Metalloproteinase (MMP)-2, MMP-9, and Membrane Type 1-MMP in Hepatocellular and Pancreatic Adenocarcinoma: Implications for Tumor Progression and Clinical Prognosis," *Clinical Cancer Research*, Jul. 2000; 6(7):2726-2734.

Mader et al., "Stabilizing effect of an S-layer on liposomes towards thermal or mechanical stress," *Biochimica et Biophysica Acta* Apr. 1999, 1418(1):106-116.

Mallik, Sanku "Collaborative Research: Echogenic Lipid Nanoparticles for Concurrent Ultrasound Imaging and Drug Delivery," Grant Abstract, Grant No. DMR 1005011 [online]. National Science Foundation, project dates Jul. 15, 2010 to Sep. 30, 2014 [retrieved on Feb. 17, 2016]. Retrieved from the Internet:<URL: http://www.nsf.gov/awardsearch/showAward?AWD_ID=1005011&HistoricalAwards=false>; 3 pgs.

Mallik, Sanku "Lipid Nanoparticle-Mediated Amplified Detection of Active Extracellular Triple Helicases," Grant Abstract, Grant No. DMR 1306154 [online]. National Science Foundation, project dates Jul. 15, 2013 to Jun. 30, 2016 [retrieved on Mar. 9, 2016]. Retrieved from the Internet:<URL: http://www.nsf.gov/awardsearch/showAward?AWD_ID=1306154&HistoricalAwards=false>; 3 pgs.

Markowitz et al., "Controlled Release from Liposomes of Long-Chain Polymerizable Diacetylenic Phosphocholine and a Short-Chain Saturated Phospholipid," In *Diagnostic Biosensor Polymers ACS Symposium Series*, vol. 556. Usmani et al. (Eds.), published by the American Chemical Society, Washington, DC, 1994. Chapter 21, pp. 264-274.

Maruyama et al., "Possibility of active targeting to tumor tissues with liposomes," *Advanced Drug Delivery Reviews*, Nov. 1999; 40(1-2):89-102.

Mayer et al., "Characterization of liposomal systems containing doxorubicin entrapped in response to pH gradients," *Biochimica et Biophysica Acta*, Jun. 1990; 1025(2):143-151.

Meers, "Enzyme-activated targeting of liposomes," *Advanced Drug Delivery Reviews*, Dec. 2001; 53(3):265-272.

Melacini et al, "Collagen-Based Structures Containing the Peptoid Residue N-Isobutylglycine (Nleu). 6. Conformational Analysis of Gly-Pro-Nleu Sequences by $^1$H NMR, CD, and Molecular Modeling," *Journal of the American Chemical Society*, 1996; 118(44):10725-10732.

Melacini et al., "Acetyl-Terminated and Template-Assembled Collagen-Based Polypeptides Composed of Gly-Pro-Hyp Sequences. 3. Conformational Analysis by $^1$H-NMR and Molecular Modeling Studies," *Journal of the American Chemical Society*, 1996; 118(43):10359-10364.

Miller et al., "Visible light-induced destabilization of endocytosed liposomes," *FEBS Letters*, Feb. 2000; 467(1):52-55.

Misek et al., "Early Detection and Biomarkers in Pancreatic Cancer," *J. Natl. Compr. Canc Netw* ., Nov. 2007; 5(10):1034-1041.

Molineux, "Pegylation: engineering improved pharmaceuticals for enhanced therapy," *Cancer Treatment Reviews*, 2002; 28(Suppl. 1):13-16.

Moribe et al., "Reviews on PEG-coated liposomal drug carriers," *Drug Delivery System*, 2001; 16(3):165-171. (English abstract included).

Mueller et al., "Visible-Light-Stimulated Destabilization of PEG-Liposomes," *Macromolecules*, 2000; 33(13):4799-4804.

Mueller et al., "Supramolecular Materials via Polymerization of Mesophases of Hydrated Amphiphiles," Chemical Reviews, Mar. 2002; 102:727-757.

Muller et al., "Heterotrimeric Collagen Peptides as Fluorogenic Collagenase Substrates: Synthesis, Conformational Properties, and Enzymatic Digestion," *Biochemistry*, May 2000; 39(17):5111-5116.

Murphy et al., "Gelatinases A and B," *Methods Enzymology*, 1995; 248:470-484.

Nagase et al., "Matrix Metalloproteinases," *The Journal of Biological Chemistry*, 1999; 274:21491-21494.

Nakagawa et al., "Expression of Type IV Collagen and Its Degrading Enzymes in Squamous Cell Carcinoma of Lung," *Japanese Journal of Cancer Research*, 1994; 85:934-938.

(56) References Cited

OTHER PUBLICATIONS

Nahire et al., "Ultrasound Enhanced Matrix Metalloproteinase-9 Triggered Release of Contents from Echogenic Liposomes," *Molecular Pharmaceutics*, Sep. 2012; 9(9):2554-2564.
Nelson et al., "Matrix Metalloproteinases: Biologic Activity and Clinical Implications," *Journal Clinical Oncology*, Mar. 2000; 18:1135-1149.
Nicolazzi et al., "Cationic Lipids for Transfection," *Current Medicinal Chemistry*, Jul. 2003; 10(14):1263-1277.
Nielsen et al., "Therapeutic efficacy of anti-ErbB2 immunoliposomes targeted by a phage antibody selected for cellular endocytosis," *Biochimica et Biophysica Acta*, 2002; 1591(1-3):109-118.
Oku, "Anticancer therapy using glucuronate modified long-circulating liposomes," *Advanced Drug Delivery Reviews*, Nov. 1999; 40(1-2):63-73.
Ottl et al., "Design and synthesis of heterotrimeric collagen peptides with a built-in cystine-knot Models for collagen catabolism by matrix-metalloproteases," *FEBS Letters*, Nov. 1996; 398(1):31-36.
Ottl et al., "A new strategy for regioselective interstrand disulfide bridging of multiple cysteine peptides," *Tetrahedron Letters*, Feb. 1999; 40(8):1487-1490.
Pak et al., "Triggerable liposomal fusion by enzyme cleavage of a novel peptide-lipid conjugate," *Biochimica et Biophysica Acta*, Jun. 1998; 1372(1):13-27.
Papadopoulou et al., "Expression of Gelatinase-A (MMP-2) in Human Colon Cancer and Normal Colon Mucosa," *Tumour Biology*, Nov.-Dec. 2001; 22(6):383-389.
Phung et al., "Rapid generation of in vitro multicellular spheroids for the study of monoclonal antibody therapy," *Journal of Cancer*, 2011; 2:507-514.
Pirila et al., "Gelatinase A (MMP-2), Collagenase-2 (MMP-8), and Laminin-5 γ2-Chain Expression in Murine Inflammatory Bowel Disease (Ulcerative Colitis)," *Digestive Diseases and Sciences*, Jan. 2003; 48(1):93-98.
Polette et al., "Gelatinase A expression and localization in human breast cancers. An in situ hybridization study and immunohistochemical detection using confocal microscopy," *Virchows Archiv*, 1994; 424(6):641-645.
Pompella et al., "The changing faces of glutathione, a cellular protagonist," *Biochemical Pharmacology*, Oct. 2003: 66(8):1499-1503.
Papahadjopoulos et al., "Sterically stabilized liposomes: Improvements in pharmacokinetics and antitumor therapeutic efficacy," *Proc. Natl. Acad. Sci. USA*, Dec. 1991; 88:11460-11464.
Papahadjopoulos et al., "Steric stabilization, an overview," In *Liposomes: Rational Design*, Janoff, A. S. (Ed.), Marcel Dekker, New York, 1999, pp. 1-12.
Pyo et al., "Targeted gene disruption of matrix metalloproteinase-9 (gelatinase B) suppresses development of experimental abdominal aortic aneurysms," *The Journal of Clinical Investigation*, Jun. 2000; 105(11):1641-1649.
Radhakrishnan et al., "Dual enzyme responsive microcapsules simulating an "OR" logic gate for biologically triggered drug delivery applications," *Chemical Communications*, Jun. 2013; 49(47):5390-5392.
Ramachandran, "Structure of collagen at the molecular level," In: *Treatise on Collagen*. Ramachandran, G. N. (Ed.), Academic Press, NY, 1967, pp. 103-183.
Ren et al., "Sheddable micelles based on disulfide-linked hybrid PEG-polypeptide copolymer for intracellular drug delivery," *Polymer*, Jul. 2011; 52(16):3580-3586.
Rich et al., "The molecular structure of collagen," *Journal of Molecular Biology*, Oct. 1961; 3(5):483-506, IN1-IN4.
Ringsdorf et al., "Molecular Architecture and Function of Polymeric Oriented Systems: Models for the Study of Organization, Surface Recognition, and Dynamics of Biomembranes," *Angewandte Chemie International Edition*, 1988; 27(1):113-158.
Ringsdorf, In *Physical Chemistry of Biological Interfaces*, Baszkin, A.; Norde, W. (Ed), Marcell Dekker, New York, NY, 2000, pp. 243-282.
Rogers et al., "The Potential of Liposomes in Oral Drug Delivery," *Critical Reviews in Therapeutic Drug Carrier Systems*, 1998; 15(5):421-480.
Saarialho-Kere, "Patterns of matrix metalloproteinase and TIMP expression in chronic ulcers," *Archives of Dermatological Research*, Jul. 1998; 290:S47-S54.
Sarkar et al., "Matrix Metalloproteinase-Assisted Triggered Release of Liposomal Contents," *Bioconjugate Chemistry*, Jan. 2008; 19(1):57-64.
Sasaki et al., "Cytotoxicity tests on eye drop preparations by LDH release assay in human cultured cell lines," *Toxicology in Vitro*, Oct. 1994; 8(5)1113-1119.
Segain et al., "Induction of Fibroblast Gelatinase B Expression by Direct Contact with Cell Lines Derived from Primary Tumor but not from Metastases," *J. Cancer Res.*, Dec. 1996; 56:5506-5512.
Sehgal et al., "Requirement for Matrix Metalloproteinase-9 (Gelatinase B) Expression in Metastasis by Murine Prostate Carcinoma," *American Journal of Pathology*, Feb. 1998; 152(2):591-596.
Seki, "Phase separation of polymerized lipids in hybrid liposomes," *Polymer Bulletin*, Jun. 1985; 13(6):489-492.
Spratt et al., "Rapid release of liposomal contents upon photoinitiated destabilization with UV exposure," *Biochimica et Biophysica Acta*, Apr. 2003; 1611(1-2):35-43.
Srivastava, D. K. "Catalysis and Inhibition of Gelatinases," Grant Abstract, Grant No. 1R01CA113746 [online]. National Institutes of Health, project dates Mar. 16, 2006 to Feb. 28, 2011 [retrieved on Feb. 17, 2016]. Retrieved from the Internet:<URL: https://projectreporter.nih.gov/pr_Prj_info_desc_dtls.cfm?aid=7033473&icde=28267 73&ddparam=&ddvalue=&ddsub=&cr=1&csb=default&cs=ASC&print=yes; 2 pgs.
Sutherland et al., "Cell and environment interactions in tumor microregions: the multicell spheroid model," *Science*, Apr. 1988; 240(4849):177-184.
Takeoka, "Phase separation of polymerized mixed liposomes: analysis of release behavior of entrapped molecules with skeletonization," *Macromolecules*, 1991; 24(6):1279-1283.
Tauro et al., "Matrix Metalloprotease Triggered Delivery of Cancer Chemotherapeutics from Hydrogel Matrixes," *Bioconjugate Chemistry*, 2005; 16(5):1133-1139.
Tiwari, "Temperature sensitive liposomes of plumbagin: characterization and in vivo evaluation in mice bearing melanoma B16F1," *J. Drug Targeting*, Dec. 2002; 10(8):585-591.
Tokuraku et al., "Activation of the precursor of gelatinase A/72 kda type IV collagenase/MMP-2 in lung carcinomas correlates with the expression of membrane-type matrix metalloproteinase (MT-MMP) and with lymph node metastasis," *International Journal of Cancer*, Oct. 1995; 64(5):355-359.
Torchilin, "Recent advances with liposomes as pharmaceutical carriers," *Nature Reviews Drug Discovery*, Feb. 2005; 4(2):145-160.
Trubetskoy, "Massage-induced release of subcutaneously injected liposome-encapsulated drugs to the blood," *Journal of Controlled Release*, Jan. 1998; 59:13-19.
Turk et al., "Characterization of a novel pH-sensitive peptide that enhances drug release from folate-targeted liposomes at endosomal pHs," *Biochimica et Biophysica Acta*, 2002; 1559:56-68.
Turner et al., "The transfection of Jurkat T-leukemic cells by use of pH sensitive immunoliposomes," *J. Liposome Res*. Feb.-May 2002; 12(1-2):45-50.
Vogel et al., "Peptide-Mediated Release of Folate-Targeted Liposome Contents from Endosomal Compartments," *Journal of the American Chemical Society*, 1996; 118(7):1581-1586.
Wan et al., "Liposomes from Novel Photolabile Phospholipids: Light-Induced Unloading of Small Molecules As Monitored by PFG NMR," *Journal of the American Chemical Society*, 2002; 124:5610-5611.
Whittaker et al., "Design and Therapeutic Application of Matrix Metalloproteinase Inhibitors," *Chemical Reviews*, Sep. 1999; 99:2735-2776.

(56) References Cited

OTHER PUBLICATIONS

Woodle, Long circulating liposomes: Old drugs, new therapies, Strom, G. (Ed.); Springer, Berlin, Germany, 1998.

Wymer et al., "Cascade Liposomal Triggering: Light-Induced $Ca^{2+}$ Release from Diplasmenylcholine Liposomes Triggers $PLA_2$-Catalyzed Hydrolysis and Contents Leakage from DPPC Liposomes," *Bioconjugate Chemistry*, May-Jun. 1998; 9:305-308.

Yingyuad et al., "Enzyme-Triggered PEGylated pDNA Nanoparticles for Controlled Release of pDNA in Tumors," *Bioconjugate Chemistry*, Mar. 2013; 24(3):343-362.

Yingyuad et al., "Enzyme-triggered PEGylated siRNA-nanoparticles for controlled release of siRNA," *J RNAi Gene Silencing*, Jan. 2014; 10:490-499.

Young et al., "Characterization of Gelatinases Linked to Extracellular Matrix Invasion in Ovarian Adenocarcinoma: Purification of Matrix Metalloproteinase 2," *Gynecol Oncol.*, Jul. 1996; 62:89-99.

Zhang et al., "Disulfide crosslinked PEGylated starch micelles as efficient intracellular drug delivery platforms," *Soft Matter*, 2013; 9(7):2224-2233.

Zhang, et al., "Interaction of Cationic Antimicrobial Peptides with Model Membranes," *J. Biol. Chem.*, Sep. 2001; 276(38):35714-35722.

SEQUENCE LISTING

<160> NUMBER OF SEQ ID NOS: 15

<210> SEQ ID NO 1
<211> LENGTH: 20
<212> TYPE: PRT
<213> ORGANISM: artificial
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp

<400> SEQUENCE: 1

Gly Pro Gln Gly Ile Ala Gly Gln Arg Gly Pro Xaa Gly Pro Xaa Gly
1               5                   10                  15

Pro Xaa Gly Gly
            20

<210> SEQ ID NO 2
<211> LENGTH: 23
<212> TYPE: PRT
<213> ORGANISM: artificial
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp

<400> SEQUENCE: 2

Gly Pro Gln Gly Ile Ala Gly Gln Arg Gly Pro Xaa Gly Pro Xaa Gly
1               5                   10                  15

Pro Xaa Gly Pro Xaa Gly Gly
            20

<210> SEQ ID NO 3
<211> LENGTH: 26
<212> TYPE: PRT
<213> ORGANISM: artificial
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES -continued

```
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp
<220> FEATURE:
<221> NAME/KEY: MOD_RES
<222> LOCATION: (24)..(24)
<223> OTHER INFORMATION: 4Hyp

<400> SEQUENCE: 3

Gly Pro Gln Gly Ile Ala Gly Gln Arg Gly Pro Xaa Gly Pro Xaa Gly
1               5                   10                  15

Pro Xaa Gly Pro Xaa Gly Pro Xaa Gly Gly
            20                  25

<210> SEQ ID NO 4
<211> LENGTH: 30
<212> TYPE: PRT
<213> ORGANISM: artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
<221> NAME/KEY: MOD_RES
<222> LOCATION: (22)..(22)
<223> OTHER INFORMATION: 4Hyp
<220> FEATURE:
<221> NAME/KEY: MOD_RES
<222> LOCATION: (25)..(25)
<223> OTHER INFORMATION: 4Hyp
<220> FEATURE:
<221> NAME/KEY: MOD_RES
<222> LOCATION: (28)..(28)
<223> OTHER INFORMATION: 4Hyp

<400> SEQUENCE: 4

Gly Gly Pro Xaa Gly Pro Xaa Gly Pro Xaa Gly Pro Gln Gly Ile Ala
1               5                   10                  15

Gly Gln Arg Gly Pro Xaa Gly Pro Xaa Gly Pro Xaa Gly Gly
            20                  25                  30

<210> SEQ ID NO 5
<211> LENGTH: 36
<212> TYPE: PRT
<213> ORGANISM: artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
```

```
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (25)..(25)
<223> OTHER INFORMATION: 4Hyp
<220> FEATURE:
<221> NAME/KEY: MOD_RES
<222> LOCATION: (28)..(28)
<223> OTHER INFORMATION: 4Hyp
<220> FEATURE:
<221> NAME/KEY: MOD_RES
<222> LOCATION: (31)..(31)
<223> OTHER INFORMATION: 4Hyp
<220> FEATURE:
<221> NAME/KEY: MOD_RES
<222> LOCATION: (34)..(34)
<223> OTHER INFORMATION: 4Hyp

<400> SEQUENCE: 5

Gly Gly Pro Xaa Gly Pro Xaa Gly Pro Xaa Gly Pro Xaa Gly Pro Gln
1               5                   10                  15

Gly Ile Ala Gly Gln Arg Gly Pro Xaa Gly Pro Xaa Gly Pro Xaa Gly
            20                  25                  30

Pro Xaa Gly Gly
        35

<210> SEQ ID NO 6
<211> LENGTH: 42
<212> TYPE: PRT
<213> ORGANISM: artificial
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: 4Hyp
<220> FEATURE:
<221> NAME/KEY: MOD_RES
<222> LOCATION: (7)..(7)
<223> OTHER INFORMATION: 4Hyp
<220> FEATURE:
<221> NAME/KEY: MOD_RES
<222> LOCATION: (10)..(10)
<223> OTHER INFORMATION: 4Hyp
<220> FEATURE:
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (16)..(16)
<223> OTHER INFORMATION: 4Hyp
<220> FEATURE:
<221> NAME/KEY: MOD_RES
<222> LOCATION: (28)..(28)
<223> OTHER INFORMATION: 4Hyp
<220> FEATURE:
<221> NAME/KEY: MOD_RES
<222> LOCATION: (31)..(31)
<223> OTHER INFORMATION: 4Hyp
<220> FEATURE:
<221> NAME/KEY: MOD_RES
<222> LOCATION: (34)..(34)
<223> OTHER INFORMATION: 4Hyp
<220> FEATURE:
<221> NAME/KEY: MOD_RES
<222> LOCATION: (37)..(37)
<223> OTHER INFORMATION: 4Hyp
<220> FEATURE:
<221> NAME/KEY: MOD_RES
<222> LOCATION: (40)..(40)
<223> OTHER INFORMATION: 4Hyp
```

-continued

```
<400> SEQUENCE: 6

Gly Gly Pro Xaa Gly Pro Xaa Gly Pro Xaa Gly Pro Xaa Gly Pro Xaa
1               5                   10                  15

Gly Pro Gln Gly Ile Ala Gly Gln Arg Gly Pro Xaa Gly Pro Xaa Gly
            20                  25                  30

Pro Xaa Gly Pro Xaa Gly Pro Xaa Gly Gly
        35                  40

<210> SEQ ID NO 7
<211> LENGTH: 14
<212> TYPE: PRT
<213> ORGANISM: artificial
<220> FEATURE:
<223> OTHER INFORMATION: Synthetic Peptide

<400> SEQUENCE: 7

Gly Pro Gln Gly Ile Ala Gly Gln Arg Gly Arg Val Gly Gly
1               5                   10

<210> SEQ ID NO 8
<211> LENGTH: 20
<212> TYPE: PRT
<213> ORGANISM: artificial
<220> FEATURE:
<223> OTHER INFORMATION: Synthetic Peptide

<400> SEQUENCE: 8

Gly Pro Gln Gly Ile Ala Gly Gln Arg Gly Pro Pro Gly Pro Pro Gly
1               5                   10                  15

Pro Pro Gly Gly
            20

<210> SEQ ID NO 9
<211> LENGTH: 23
<212> TYPE: PRT
<213> ORGANISM: artificial
<220> FEATURE:
<223> OTHER INFORMATION: Synthetic Peptide

<400> SEQUENCE: 9

Gly Pro Gln Gly Ile Ala Gly Gln Arg Gly Pro Pro Gly Pro Pro Gly
1               5                   10                  15

Pro Pro Gly Pro Pro Gly Gly
            20

<210> SEQ ID NO 10
<211> LENGTH: 26
<212> TYPE: PRT
<213> ORGANISM: artificial
<220> FEATURE:
<223> OTHER INFORMATION: Synthetic Peptide

<400> SEQUENCE: 10

Gly Pro Gln Gly Ile Ala Gly Gln Arg Gly Pro Pro Gly Pro Pro Gly
1               5                   10                  15

Pro Pro Gly Pro Pro Gly Pro Pro Gly Gly
            20                  25

<210> SEQ ID NO 11
<211> LENGTH: 30
<212> TYPE: PRT
<213> ORGANISM: artificial
<220> FEATURE:
<223> OTHER INFORMATION: Synthetic Peptide
```

-continued

<400> SEQUENCE: 11

Gly Gly Pro Pro Gly Pro Pro Gly Pro Pro Gly Pro Gln Gly Ile Ala
1               5                   10                  15

Gly Gln Arg Gly Pro Pro Gly Pro Pro Gly Pro Pro Gly Gly
            20                  25                  30

<210> SEQ ID NO 12
<211> LENGTH: 36
<212> TYPE: PRT
<213> ORGANISM: artificial
<220> FEATURE:
<223> OTHER INFORMATION: Synthetic Peptide

<400> SEQUENCE: 12

Gly Gly Pro Pro Gly Pro Pro Gly Pro Pro Gly Pro Pro Gly Pro Gln
1               5                   10                  15

Gly Ile Ala Gly Gln Arg Gly Pro Pro Gly Pro Pro Gly Pro Pro Gly
            20                  25                  30

Pro Pro Gly Gly
        35

<210> SEQ ID NO 13
<211> LENGTH: 42
<212> TYPE: PRT
<213> ORGANISM: artificial
<220> FEATURE:
<223> OTHER INFORMATION: Synthetic Peptide

<400> SEQUENCE: 13

Gly Gly Pro Pro Gly Pro Pro Gly Pro Pro Gly Pro Pro Gly Pro Pro
1               5                   10                  15

Gly Pro Gln Gly Ile Ala Gly Gln Arg Gly Pro Pro Gly Pro Pro Gly
            20                  25                  30

Pro Pro Gly Pro Pro Gly Pro Pro Gly Gly
        35                  40

<210> SEQ ID NO 14

<400> SEQUENCE: 14

000

<210> SEQ ID NO 15
<211> LENGTH: 21
<212> TYPE: PRT
<213> ORGANISM: artificial
<220> FEATURE:
<223> OTHER INFORMATION: Synthetic Peptide
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (15)..(15)
<223> OTHER INFORMATION: 4Hyp
<220> FEATURE:
<221> NAME/KEY: MOD_RES
<222> LOCATION: (18)..(18)
<223> OTHER INFORMATION: 4Hyp
<220> FEATURE:
<221> NAME/KEY: MOD_RES
<222> LOCATION: (21)..(21)
<223> OTHER INFORMATION: 4Hyp

<400> SEQUENCE: 15

```
Gly Pro Leu Gly Leu Ala Arg Lys Gly Gly Pro Xaa Gly Pro Xaa Gly
1               5                   10                  15

Pro Xaa Gly Pro Xaa
            20
```

CONTROLLED RELEASE NANOPARTICLES AND METHODS OF USE

CROSS-REFERENCE TO RELATED APPLICATIONS

This application claims the benefit of U.S. Provisional Application Ser. No. 62/015,213, filed Jun. 20, 2014, which is incorporated by reference herein.

SEQUENCE LISTING

This application contains a Sequence Listing electronically submitted via EFS-Web to the United States Patent and Trademark Office as an ASCII text file entitled "25500440101_ST25.txt" having a size of 8 kilobytes and created on Sep. 15, 2015. The information contained in the Sequence Listing is incorporated by reference herein.

GOVERNMENT FUNDING

This invention was made with government support under 1R01CA113746, awarded by the National Institutes of Health, DMR1005011, awarded by the National Science Foundation, and DMR1306154, awarded by the National Science Foundation. The government has certain rights in the invention.

BACKGROUND

Various drug carriers (e.g., liposomes, polymers, microspheres, antibody-drug conjugates) have been developed to alter the bio-distribution and pharmacokinetic properties of drug molecules. Among such carriers, liposomes offer several advantages as clinical drug delivery vehicles, and at present, there are 13 liposome-mediated drug delivery systems approved for the treatment of a variety of human diseases (e.g., breast cancer, ovarian cancer, meningitis, fungal infections, leukaemia, and others) (Torchilin, Nat. Rev. Drug Discovery, 2005, 4, 145-160). In addition, the liposome mediated delivery of about 30 other small molecule drugs, DNA fragments, and diagnostic compounds are currently at different stages of clinical trials (Felnerova et al., Curr. Opin. Biotechnol, 2004, 15, 518-529). In recent years, liposomes have also been tested as vehicles for gene delivery in approaches for treating human diseases (M. C. de Lima et al., Current Medicinal Chemistry, 2003, 10, 1221-1231; C. Nicolazzi et al., Current Medicinal Chemistry, 2003, 10, 1263-1277; V. Kumar et al., A. Current Medicinal Chemistry, 2003, 10, 1297-1306; S. Li et al., Liposomes: Rational Design; Janoff, A. S. (Ed.), Marcel Dekker, New York, 1999, pp. 89-124).

Many drugs, especially the anti-cancer drugs, cause severe and sometimes life-threatening side effects. Liposomes have been used to reduce these undesirable side effects. Liposomal doxorubicin and other anthracyclin formulations have been approved for clinical use (A. Gabizon et al., Liposomes: Rational Design; Janoff, A. S. (Ed.), Marcel Dekker, New York, 1999, pp. 343-362). These formulations show many advantages, viz., prolonged circulation times, protection of key organs against toxicity, and accumulation of liposome-encapsulated drugs in solid tumors (A. Gabizon et al., Liposomes: Rational Design; Janoff, A. S. (Ed.), Marcel Dekker, New York, 1999, pp. 343-362). In order to achieve selective targeting, recognition moieties are attached to the outer surface of the liposomes. The targeting group can be an antibody, (G. A. Koning et al., Cancer Detection Prevention 2002, 26, 299-307; U. B. Nielson et al., Biochim. Biophys. Acta, 2002, 1591, 109-118; C. Turner et al., S. J. Liposome Res. 2002, 12, 45-50; R. Banerjee, J. Biomaterials Applications, 2001, 16, 3-21) (K. Maruyama et al., Adv. Drug Delivery Rev., 1999, 40, 89-102; N. Oku, Adv. Drug Delivery Rev., 1999, 40, 63-73; D. D. Lasic, Tibtech, 1998, 16, 307-321) a peptide, (L. Zhang, et al., J. Biol. Chem., 2001, 276, 35714-35722; K. Vogel et al., J. Am. Chem. Soc., 1996, 118, 1581-1586) or small molecules, (A. Gabizon et al., S. Adv. Drug. Delv. Rev., 2004, 56, 1177-1192; C. P. Leamon et al., Adv. Drug. Delv. Rev., 2004, 56, 1127-1141) which target specific receptors.

Usually upon targeting, the encapsulated drugs are released passively to the selected tissue sites. This is based on the transport property of the molecules across the lipid bilayers of liposomes. Triggered release of drugs and labeled molecules from liposomes has been recognized to be an attractive therapeutic approach. In this approach of drug delivery, the liposomes, particularly non-polymerizable liposomes, which are most frequently used as the drug delivery vehicles, do not release contents until the membranes are destabilized by the external agents (trigger). The trigger can be a change in pH (M. F. Francis et al., Biomacromolecules, 2001, 2, 741-749; D. C. Drummond et al., Progress Lipid Res., 2000, 39, 409-460; M. J. Turke et al., Biochim. Biophys. Acta., 2002, 1559, 56-68; J. A. Boomer et al., Langmuir, 2003, 19, 6408-6415), mechanical stress (N. Karoonuthaisiri et al., Colloids and Surfaces, B: Biointerfaces, 2003, 27, 365-375; C. Mader et al., Biochim. Biophys. Acta, 1999, 1418, 106-116; V. S. Trubetskoy, J. Controlled Release, 1998, 59, 13-19), metal ions, (S. C. Davis et al., Bioconj. Chem., 1998, 9, 783-792) temperature (S. B. Tiwari, J. Drug Targeting, 2002, 10, 585-591; P. Chandaroy et al., J. Controlled Release, 2001, 76, 27-37; H. Hayashi et al., Bioconj. Chem., 1999, 10, 412-418), light (Z. Li et al., Langmuir, 2003, 19, 6381-6391; Y. Wan et al., J. Am. Chem. Soc., 2002, 124, 5610-5611; C. R. Miller et al., FEBS Letters, 2000, 467, 52-5; M. Babincova et al., J. Magnetism Magnetic Mater., 1999, 194, 163-166), or enzymes such as elastase (P. Meers, Adv. Drug Deliv. Reviews, 2001, 53, 265-272), alkaline phosphatase (L. Zhang et al., J. Biol. Chem., 2001, 276, 35714-35722; K. Vogel et al., J. Am. Chem. Soc., 1996, 118, 1581-1586), trypsin (C. C. Pak et al., Biochim. Biophys. Acta, 1998, 1372, 13-27), and phospholipase $A_2$ (N. Seki, Polym. Bull., 1985, 13, 489-492; S. Takeoka, Macromolecules, 1991, 24, 1279-1283; H. Ringsdorf, Physical Chemistry of Biological Interfaces, Baszkin, A.; Norde, W. (Ed), Marcell Dekker, New York, N.Y., 2000, pp. 243-282; H. Ringsdorf et al., Angew. Chem. Intl. Ed. Engl., 1988, 27, 114-158, L. Hu et al., Biochem. Biophys. Res. Commun., 1998, 141, 973-978; J. Davidsen et al., Int. J. Pharm., 2001, 214, 67-69; J. Davidsen et al., Biochim. Biophys. Acta, 2003, 1609, 95-101). Conformational changes of peptides, induced by the change in pH, have also been used to facilitate the content release from liposomes (M. J. Turke et al., Biochim. Biophys. Acta., 2002, 1559, 56-68; J. A. Boomer et al., Langmuir, 2003, 19, 6408-6415). Two agents (light and enzymes; light and pH change) acting in sequence have been used as the liposomal triggers (O. V. Gerasimov et al., Advanced Drug Delivery Reviews, 1999, 38, 317-338; N. J. Wymer et al., Bioconj. Chem., 1998, 9, 305-308). When the liposomes are conjugated to an antibody (M. F. Francis et al., Biomacromolecules, 2001, 2, 741-749; D. C. Drummond et al., Progress Lipid Res., 2000, 39, 409-460; M. J. Turke et al., Biochim. Biophys. Acta., 2002, 1559, 56-68; J. A.

Boomer et al., Langmuir, 2003, 19, 6408-6415) or a suitable ligand (M. J. Turke et al., Biochim. Biophys. Acta., 2002, 1559, 56-68; L. Zhang et al., J. Biol. Chem., 2001, 276, 35714-35722; K. Vogel et al., J. Am. Chem. Soc., 1996, 118, 1581-1586), both active targeting and triggered release can be achieved at the site of choice.

Hybrid liposomes polymerized with domains of non-polymerizable lipids have been used as the carriers when slow and controlled release of the entrapped molecules (dyes) are required (M. A. Markowitz et al., Diagnostic Biosensor Polymers, American Chemical Society, Washington, D.C., 1994, pp. 264-274). In hybrid liposomes, the non-polymerizable lipids phase-separate, during the polymerization process, forming separate lipid domains (N. Seki et al., Polym. Bull., 1985, 13, 489-492; S. Takeoka et al., Macromolecules, 1991, 24, 1279-1283; H. Ringsdorf, Physical Chemistry of Biological Interfaces, Baszkin, A.; Norde, W. (Ed), Marcell Dekker, New York, N.Y., 2000, pp. 243-282; H. Ringsdorf et al., Angew. Chem. Intl. Ed. Engl., 1988, 27, 114-158). The amount of non-polymerizable lipids can be adjusted to control the rate of release of the entrapped molecules (S. Takeoka et al., Macromolecules, 1991, 24, 1279-1283). Hybrid liposomes can be selectively opened at the non-polymerized domains ("uncorking" of the liposomes) using a detergent, a suitable chemical (reducing or oxiding agents) or an enzyme (e.g., $PLA_2$) (H. Ringsdorf, Physical Chemistry of Biological Interfaces, Baszkin, A.; Norde, W. (Ed), Marcell Dekker, New York, N.Y., 2000, pp. 243-282). The resultant liposomes with "holes" retain the spherical structure and rapidly release their contents to the outside media (H. Ringsdorf, Physical Chemistry of Biological Interfaces, Baszkin, A.; Norde, W. (Ed), Marcell Dekker, New York, N.Y., 2000, pp. 243-282).

There are reports in the literature of photo-initiated destabilization of the hybrid liposomes (A. Mueller et al., Macromolecules, 2000, 33, 4799-4804; B. Bondurant et al., J. Am. Chem. Soc., 1998, 120, 13541-13542; D. E. Bennett et al., Biochemistry, 1995, 34, 3102-3113). These liposomes are composed of polymerizable lipids (containing conjugated dienes at the end of the hydrophobic chains) and saturated lipids. The liposomes rapidly release their contents, when exposed to the UV light, during the polymerization process (T. Spratt et al., Biochim. Biophys. Acta, 2003, 1611, 35-43). The literature reports indicate that the hybrid liposomes are either stabilized or destabilized by polymerizations, depending on the structures of the polymerizable lipids (A. Mueller et al., Chem. Rev., 2002, 102, 727-757).

Unpolymerized as well as polymerized liposomes, after intravenous administration, are rapidly recognized by the phagocytic cells of the reticuloendethelial system. As a result, the liposomes are removed from blood stream and accumulate mostly in liver and spleen within a few minutes to a few hours after injection (D. Ppahadjopous et al., Liposomes: Rational Design, Janoff, A. S. (Ed.), Marcel Dekker, New York, 1999, pp. 1-12). In order to promote long circulation times to liposomes, small amounts (<10%) of polymerizable diacyl phosphatidyl inositol has been incorporated into liposomes (D. Ppahadjopous et al., Liposomes: Rational Design, Janoff, A. S. (Ed.), Marcel Dekker, New York, 1999, pp. 1-12). Incorporation of polyethylene glycol conjugated lipids in the liposomes (stealth liposomes) is an alternative strategy to achieve long circulation times (T. Ishida et al., Biosciences Reports, 2002, 22, 197-224; M. C. Woodle, Long circulating liposomes: Old drugs, new therapies, Strom, G. (Ed.); Springer, Berlin, Germany, 1998).

Unpolymerized liposomes are typically not stable in the gastro-intestinal tract; hence, most of the studies on liposomal delivery rely on the intravenous administration of the drug formulations. However, polymerized liposomes maintain their integrity in the GI tract, and a portion of the administered dose (<10%) gets transported into the systemic circulation (J. Rogers et al., Critical Rev. Therapeutic Drug Carrier Sys., 1998, 16, 421-480). Blood vessels of tumors are inherently leaky due to wider inter-endothelial junctions, large number of fenestrae and discontinuous (or absent) basement membranes (H. F. Dvorak et al., Am. J. Pathol., 1988, 133, 95-109). The openings can be up to 400 nm in diameter. Due to such an increase in vascular permeability, liposomes (of diameter 100 nm or less) are known to accumulate in soft or even in solid tumors (K. Maruyama et al., Adv. Drug Delivery Rev., 1999, 40, 89-102; N. Oku, Adv. Drug Delivery Rev., 1999, 40, 63-73; D. D. Lasic, Tibtech, 1998, 16, 307-321).

Of four major classes of ECM degrading enzymes (viz., cysteine proteases, aspartic proteases, serine proteases, and metalloproteases,), matrix metalloproteases (MMPs) have been implicated in several diseases. Based on the structural features (including the amino acid sequences, domain organizations), 26 different types of MMPs have been recognized in human tissues, which fall into six major classes: (i) collagenases, (ii) gelatinases, (iii) stromelysins and stromelysin like MMPs, (iv) matrilysins, (v) membrane type MMPs, and (vi) other MMPs (viz., MMP-20, MMP-23, and MMP-28) (M. Whittaker et al., Chem. Rev., 1999, 99, 2735-2776; G. Murphy et al., Methods Enzymol., 1995, 248, 470-484; R. Kiyama et al., J. Med. Chem., 1999, 42, 1723-1738). Although many of these MMPs have been implicated in different types of human diseases, gelatinase-A (MMP-2) and gelatinase-B (MMP-9) have been widely recognized to be involved in the progression and metastasis in most of the human tumors. Gelatinase-A and -B have been found to be overexpressed in breast tumors (M. Polette et al., Virchows Arch Int. J. Pathol., 1994, 424, 641-645; K. Dalberg et al., World J Surg., 2000, 24, 334-340; R. Hanemaaijer et al., Int J Cancer, 2000, 86, 204-207), colorectal tumors (S. Papadopoulou et al., Tumour Biol., 2001, 22, 383-9; JP Segain et al., J. Cancer Res., 1996, 56, 5506-12), lung tumors, (M. Tokuraku et al., Int J Cancer., 1995, 64, 355-359; H. Nagawa et al., S. Jap. J. Cancer Res., 1994, 85, 934-938), prostate tumors (G. Sehgal et al., Am. J. Pathol., 1998, 152, 591-596), pancreatic tumors (T. Koshiba et al., Surg Today., 1997, 27, 302-304; T M Gress et al., Int J Cancer., 1995, 62, 407-413), and ovarian tumors (T N Young et al., Gynecol Oncol., 1996, 62, 89-99). In fact, the initial discovery of the involvement of MMPs in melanoma cancer and metastasis were ascribed to be due to the overexpression of gelatinase-A and -B (V. Kahari et al., Exp. Dermatol., 1997, 6, 199-213; U. Saarialho-K, Arch. Dermatol., 1998, 294, S47-S54; H. Nagase et al., J. Biol. Chem., 1999, 274, 21491-21494; E. Kerkela et al., Exp. Dermatol., 2003, 12, 109-125; A. R. Nelson et al., J. Clin. Oncol., 2000, 18, 1135-1149; L. A. Liotta et al., Nature, 1980, 284, 67-68).

Aside from the roles of gelatinase-A and -B in tumorigenesis and metastasis in different human tissues, these enzymes have also been found to be involved in other human diseases, such as gouty arthritis (M S Hsieh et al., J Cell Biochem., 2003, 89, 791-799), inflammatory bowel disease (ulcerative colitis) (E. Pirila et al., Dig Dis Sci., 2003, 48, 93-98), abdominal aortic aneurysms (R. Pyo et al., J Clin Invest., 2000, 105, 1641-1649), quiescent Crohn's Disease (A E Kossakowska et al., Ann N Y Acad Sci., 1999, 878, 578-580), glaucoma (C. Kee et al., J Glaucoma., 1999 8, 51-55), and sunlight induced premature skin aging (G J Fisher et al., Curr Opin Rheumatol., 2002, 14, 723-726). Evidently, gelatinase-A and -B exhibit one of the most diverse pathogenic roles, and consequently involved in causing a variety of human diseases, as compared to many other enzymes in the physiological system.

SUMMARY OF THE APPLICATION

Provided herein are nanoparticles that include a lipid layer and a compartment surrounded by the lipid layer. In one embodiment, the lipid layer includes a first lipid and a lipoprotein. The first lipid may include a POPE lipid covalently attached to a hydrophilic polymer by a disulfide bond, and the lipoprotein may include a trigger protein. The concentration of the first lipid may be between 1 mole percent (mol %) and 30 mol %. The disulfide bond of the first lipid is stable under conditions that include 10% human serum and is broken under conditions that include 50 micromolar glutathione.

The lipid layer may further include a membrane stabilizer, such as cholesterol hemisuccinate. The hydrophilic polymer may include a poly(ethyleneglycol) (PEG) molecule, and in one embodiment, the PEG molecule has an average molecular weight of at least 1800. The nanoparticle of may further include a second unsaturated lipid, such as, but not limited to, DOPC, DSPC, POPE, or DSPE. The second lipid may be unsaturated.

In one embodiment, the trigger protein includes an amino acid repeat region, such as (GPX)n, where X is 4-hydroxyproline or proline, and n is at least 3. In one embodiment, the trigger protein includes a peptide bond that is cleaved by a gelatinase, such as a gelatinase-B protease, or a member of the ADAM family of proteases, such as ADAM10 protease. When the protease is a member of the ADAM family of proteases, such as ADAM10 protease, the trigger protein may include an amino acid sequence GPL GLA RKG (GPO)$_4$ (SEQ ID NO:15).

In one embodiment, the compartment includes a compound. In one embodiment, the compound is an inhibitor of a gelatinase or a member of the ADAM family of proteases. In one embodiment, the compound is a therapeutic agent, and in another embodiment, the compound is a non-therapeutic agent, such as an imaging agent.

In one embodiment, a nanoparticle that includes a lipid layer and a compartment surrounded by the lipid layer has a lipid layer that includes a first lipid and a lipoprotein. The first lipid is covalently attached to a hydrophilic polymer by a disulfide bond, and the lipoprotein includes a trigger protein. The trigger protein includes a peptide bond that is cleaved by a member of the ADAM family of proteases, such as ADAM10 protease. In one embodiment, the trigger protein includes an amino acid sequence GPL GLA RKG (GPO)$_4$ (SEQ ID NO:15). The concentration of the first lipid may be between 1 mole percent (mol %) and 30 mol %. The disulfide bond of the first lipid is stable under conditions that include 10% human serum and is broken under conditions that include 50 micromolar glutathione.

The lipid layer may further include a membrane stabilizer, such as cholesterol hemisuccinate. The hydrophilic polymer may include a poly(ethyleneglycol) (PEG) molecule, and in one embodiment, the PEG molecule has an average molecular weight of at least 1800. The nanoparticle of may further include a second unsaturated lipid, such as, but not limited to, DOPC, DSPC, POPE, or DSPE. The second lipid may be unsaturated.

In one embodiment, the compartment includes a compound. In one embodiment, the compound is an inhibitor of a member of the ADAM family of proteases. In one embodiment, the compound is a therapeutic agent, and in another embodiment, the compound is a non-therapeutic agent, such as an imaging agent.

Also provided is a composition that includes a nanoparticle described herein and a pharmaceutically acceptable carrier.

Further provided are methods for using the nanoparticles described herein. In one embodiment, a method is for delivering a compound to an environment. The method includes providing a nanoparticle described herein, and exposing the nanoparticle to an environment that includes a (i) reducing agent at a concentration sufficient to break the disulfide bond, and (ii) an enzyme that cleaves a peptide bond of the trigger protein. Exposure of the nanoparticle to the environment results in release of the compound from the compartment. In one embodiment, the environment is an in vivo environment.

In one embodiment, a method is for inhibiting activity of an enzyme. The method includes providing a nanoparticle described herein, where the compartment includes an inhibitor of an enzyme, and exposing the nanoparticle to an environment that includes the enzyme and a reducing agent at a concentration of at least 50 micromolar, where the disulfide bond is broken in the presence of the reducing agent, and the enzyme cleaves the trigger protein to release the inhibitor. In one embodiment, the enzyme and the reducing agent are present in vivo. In one embodiment, the enzyme is a gelatinase or a member of the ADAM family of the ADAM family of proteases.

In one embodiment, a method is for treating a disease. The method includes administering to a patient having a tumor an effective amount of a composition that includes a nanoparticle described herein, wherein the compartment includes a therapeutic agent, and decreasing a symptom of the disease. In one embodiment, the symptom decreased is presence or size of the tumor.

DETAILED DESCRIPTION OF ILLUSTRATIVE EMBODIMENTS

Figure 1:
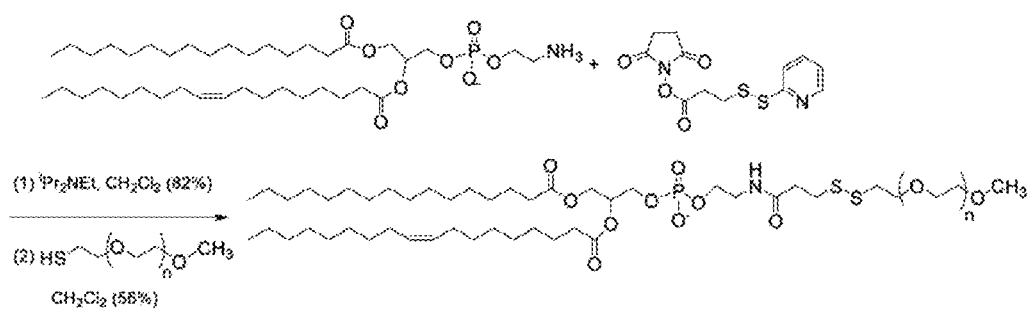
FIG. 1. Synthetic scheme for POPE-SS-PEG.

The provided herein are nanoparticles that can release their contents under specific conditions. Examples of nanoparticles include, but are not limited to, liposomes, micelles, reverse micelles, lipid conjugated nanoparticles, and nanoemulsions. A nanoparticle may include a lipid bilayer or a lipid monolayer that encloses an interior compartment that is aqueous or non-aqueous. The interior compartment makes the nanoparticle useful as tool for delivery of one or more compounds (e.g., the encapsulated cargo).

Nanoparticles may have a broad size distribution. In embodiments where the nanoparticles are liposomes, the nanoparticles have a diameter that ranges from 70 nm to 100 nm. In one embodiment, the nanoparticles have a size of 80 nm to 90 nm.

In one embodiment, a nanoparticle includes at least one type of lipid and a lipoprotein that includes a trigger protein. In one embodiment, a nanoparticle includes at least two types of lipids, and a lipoprotein that includes a trigger protein. In one embodiment, a nanoparticle also includes a membrane stabilizer.

A lipid present in a nanoparticle includes a hydrophobic tail and a hydrophilic head. A hydrophobic tail of a lipid that is useful herein has the following structure: $CH_3(CH_2)_n$, with n of at least 14 and no greater than 20, and where the end of the molecule is covalently bound to the hydrophilic head. A nanoparticle may include 1, 2, or 3 hydrocarbon chains, and each chain may be independently saturated or include unsaturated carbon-carbon bonds.

In one embodiment, the lipid (also referred to herein as a first lipid) present in a nanoparticle may be, for instance, DSPE (1,2-distearoyl-sn-glycero-3-phosphoethanolamine), DMPE (1,2-dimyristoyl-sn-glycero-3-phosphoethanolamine), DPPE (1,2-dipalmitoyl-sn-glycero-3-phosphoethanolamine), DLPE (1,2-dilauroyl-sn-glycero-3-phosphoethanolamine), DOPC (1,2-dioleoyl-sn-glycero-3-phosphocholine), DSPC (1,2-distearoyl-sn-glycero-3-phosphocholine), POPE (1-palmitoyl-2-oleoyl-sn-glycero-3-phosphoethanolamine), cholesterol, oleic acid, hexenoic acid. In one embodiment, the lipid in the liposome bilayer is DSPC (1,2-distearoyl-sn-glycero-3-phosphocholine). In one embodiment, the first lipid present in a nanoparticle is POPE (1-palmitoyl-2-oleoyl-sn-glycero-3-phosphoethanolamine).

The first lipid is covalently attached to a synthetic or natural hydrophilic polymer that can impart stealth characteristics to a nanoparticle. Suitable hydrophilic polymers may include, without limitation, poly(ethylene glycol) (PEG), poly(N-isopropylacrylamide) (PNIPAM), polyacrylamide (PAM), poly(2-oxazoline), polyethylenimine (PEI), poly(acrylic acid), polymethacrylate and other acrylic polymers, poly(vinyl alcohol) (PVA) and copolymers, and poly (vinylpyrrolidone) (PVP) and copolymers.

In some embodiments the hydrophilic polymer includes poly(ethylene glycol) (PEG). PEG has been found to be nontoxic and is approved by the FDA for use as excipients or as a carrier in different pharmaceutical formulations, foods, and cosmetics (Fuertges et al., 1990 *Journal of Controlled Release*, 11:139). PEG is a chemical compound composed of repeating ethylene glycol units and has the structure of $H—(O—CH_2—CH_2)_n—OH$ where n may be any whole number. PEGs are typically characterized by MW. For example, "$PEG_{1900}$" typically denotes a preparation that includes a mixture of oligomers having an average MW 1900. In some embodiments, PEG may have an average MW of at least 800 to no greater than 7000. For example, PEG may have a MW of at least 600 ($PEG_{600}$), at least 800 ($PEG_{800}$), at least 1000 ($PEG_{1000}$), at least 1100 ($PEG_{1100}$), at least 1200 ($PEG_{1200}$), at least 1300 ($PEG_{1300}$), at least 1400 ($PEG_{1400}$), at least 1500 ($PEG_{1500}$), at least 1600 ($PEG_{1600}$), at least 1700 ($PEG_{1700}$), at least 1800 ($PEG_{1800}$), or at least 1900 ($PEG_{1900}$). For example, PEG may have a MW of no greater than 7000 ($PEG_{7000}$), no greater than 6000 ($PEG_{6000}$), no greater than 5000 ($PEG_{5000}$), no greater than 4000 ($PEG_{4000}$), no greater than 3000 ($PEG_{3000}$), no greater than 2000 ($PEG_{2000}$), or no greater than 1900 ($PEG_{1900}$).

A synthetic or natural hydrophilic polymer imparts stealth characteristics to a nanoparticle if it decreases clearance of the nanoparticle from the circulatory system compared to a nanoparticle that does not include the hydrophilic polymer.

The covalent bond between the first lipid and the synthetic or natural hydrophilic polymer, such as PEG, is one that can be broken in the physiological environment present in the extracellular matrix of a tumor. An example of such a covalent bond is a thiol-sensitive bond, such as a disulfide bond. A thiol-sensitive bond is maintained under certain conditions and is broken (e.g., cleaved) under other conditions, such as reducing conditions.

A molecule that has a first lipid bound to PEG by a thiol-sensitive bond, such as a disulfide bond, is referred to herein as lipid-S—S-PEG. The thiol-sensitive linkage is attached to the hydrophilic head of the first lipid. A lipid-S—S-PEG molecule may be present in a nanoparticle at a concentration of at least 1 mole percent (mol %) to no greater than 30 mol %. In one embodiment, a lipid-S—S-PEG molecule is present in a nanoparticle at a concentration of at least 1 mole percent (mol %), at least 3 mol %, at least 5 mol %, at least 7 mol %, at least 10 mol %, or at least 20 mol %. In one embodiment, a lipid-S—S-PEG molecule is present in a nanoparticle at a concentration of no greater than 30 mole percent (mol %), no greater than 20 mol %, no greater than 10 mol %, no greater than 7 mol %, no greater than 5 mol %, or no greater than 3 mol %.

In those embodiments where a second lipid is present in a nanoparticle, the second lipid may be essentially any saturated or unsaturated lipid that is natural or synthetic. Examples of such lipids include, but are not limited to, DOPC (1,2-dioleoyl-sn-glycero-3-phosphocholine), DSPC (1,2-distearoyl-sn-glycero-3-phosphocholine), DSPE (1,2-distearoyl-sn-glycero-3-phosphoethanolamine), and POPE. In one embodiment, the second lipid, or combination of second lipids, may be present in a nanoparticle at a concentration of least 40 mol % to no greater than 95 mol %. In one embodiment, the second lipid, or combination of second lipids, is present in a nanoparticle at a concentration of at least 40 mole percent (mol %), at least 50 mol %, at least 60 mol %, at least 70 mol %, or at least 80 mol %. In one embodiment, the second lipid, or combination of second lipids, is present in a nanoparticle at a concentration of no greater than 95 mole percent (mol %), no greater than 90 mol %, no greater than 80 mol %, no greater than 70 mol %, no greater than 60 mol %, or no greater than 50 mol %.

Useful lipoproteins have the structure $H_3C-(CH_2)_n-$, wherein n is at least 14 to no greater than 20, and where the end of the molecule is covalently bound to a trigger protein. In one embodiment the hydrophobic tail of a lipoprotein is saturated. A lipid layer may include more than one type of lipoprotein. Examples of lipids that may be used as part of a lipoprotein include, but are not limited to, stearic acid, hexenoic acid, oleic acid, and the like.

The trigger protein is present on the surface of the nanoparticle, bound to the lipoprotein. A trigger protein includes a peptide bond that is cleaved by a protease. As used herein, the term "protein" refers broadly to a polymer of two or more amino acids joined together by peptide bonds. The term "protein" also includes molecules which contain more than one protein joined by a disulfide bond, or complexes of polypeptides that are joined together, covalently or noncovalently, as a multimer (e.g., a trimer, including a trimer that forms a triple helix). Thus, the terms peptide, oligopeptide, and polypeptide are all included within the definition of protein and these terms are used interchangeably.

Typically, a peptide bond that is cleaved by a protease is part of a recognition site that is recognized by a specific protease. In one embodiment, the recognition site identified by a protease is present on a single linear polypeptide. Examples of proteases that identify a recognition site present on a single linear protein include, but are not limited to, trypsin, chymotrypsin, and papain. In one embodiment, a trigger protein includes an amino acid sequence that, upon interaction with two other trigger proteins, forms a triple helical conformation. The triple-helical conformation can be made up of three indentical, two identical, or three different proteins. The three proteins making up a triple helix may each be joined to separate lipoproteins or may be bound to the same lipoprotein. In one embodiment, the triple helix is the structure found in natural type IV collagen; three left-handed poly proline-II-type chains supercoiled in a right-handed manner about a common axis (see Rich and Crick, *J. Mol. Biol.*, 1961, 3, 483-506, and Ramachandran, In: treatise on collagen. Ramachandran, G. N. (Ed.), Academic Press, NY, 1964, 103-183).

A trigger protein may include an amino acid repeat region. As used herein, an amino acid "repeat region" is $(Gly-X-Y)_m$, also referred to herein as $(GXY)_m$, where X is proline or a homolog thereof, preferably proline, Y is proline or 4-hydroxyproline or a homolog thereof, preferably proline or 4-hydroxyproline, and m is at least 3. Thus, in one embodiment, $(GXY)_m$, is $(GPY)_m$. A repeat region in a protein can be GPP, GPO (where O is 4-hydroxyproline), or a combination thereof. This repeat region can be present more than once in the trigger protein, and when it is present more than once the two repeat regions are typically separated by 3 or more amino acids. Without intending to be limiting, it is the repeating sequence that is believed to cause the formation of a triple helix.

In one embodiment, the protease is one that recognizes its cleavage site when the site is present in a protein having a triple helical conformation. An example of a protease that identifies a recognition site present in a trigger protein having a triple helical configuration includes collagenases and members of the ADAM family of proteases. Examples of the ADAM family are those that play a role in cancer, including ADAM10 and ADAM17. Another example is a matrix metalloprotease (MMP), a type of extracellular matrix degrading enzyme. There are at least six major classes of MMPs: (i) collagenases (MMP1, MMP-8, and MMP-13), (ii) gelatinases (MMP-2 and MMP-9), (iii) stromelysins and stromelysin-like MMPs (MMP-3, MMP-10, and MMP-11), (iv) matrilysins (MMP-7), (v) membrane type MMPs (MMP-14, MMP-15, MMP-16, and MMP-17), and (vi) other MMPs (MMP-20, MMP-23, and MMP-28) (see Fan et al., J. *Biochemistry*, 1993, 32, 13299-13309, Kramer et al., *J. Mol. Biol.*, 2001, 311, 131-147, and Kramer et al., *J. Mol. Biol.*, 2000, 301, 1191-1205).

In one embodiment the protease is gelatinase-A or gelatinase-B. An example of a gelatinase-A is available at Genbank accession number BC002576, and an example of a gelatinase-B is available at Genbank accession number BC006093. The peptide bond cleaved by gelatinase-A or gelatinase-B is the bond between glycine-leucine and between glycine-isoleucine, thus in some embodiments the trigger protein includes the amino acid sequence glycine-leucine and/or glycine-isoleucine. Examples of trigger proteins that are expected to form a triple helical conformation and include the enzymatic trigger of gelatinase-A and/or gelatinase-B include the following: GPQ GIA GQR $(GPO)_3$ GG (SEQ ID NO:1), GPQ GIA GQR $(GPO)_4$ GG (SEQ ID NO:2), GPQ GIA GQR $(GPO)_5$ GG (SEQ ID NO:3), G $(GPO)_3$ GPQ GIA GQR $(GPO)_3$ GG (SEQ ID NO:4), G $(GPO)_4$ GPQ GIA GQR $(GPO)_4$ GG (SEQ ID NO:5), G $(GPO)_5$ GPQ GIA GQR $(GPO)_5$ GG (SEQ ID NO:6), GPQ GIA GQR GRV GG (SEQ ID NO:7), GPQ GIA GQR (GPP)$_3$ GG (SEQ ID NO:8), GPQ GIA GQR (GPP)$_4$ GG (SEQ ID NO:9), GPQ GIA GQR (GPP)$_5$ GG (SEQ ID NO:10), G (GPP)$_3$ GPQ GIA GQR (GPP)$_3$ GG (SEQ ID NO:11), G (GPP)$_4$ GPQ GIA GQR (GPP)$_4$ GG (SEQ ID NO:12), G (GPP)$_5$ GPQ GIA GQR (GPP)$_5$ GG (SEQ ID NO:13), where 0 is 4-hydroxyproline, and homologs thereof.

In one embodiment the protease is ADAM10. An example of an ADAM10 protease is available at Genbank accession number BC002576. Examples of trigger proteins that are expected to form a triple helical conformation and include the enzymatic trigger of ADAM10 include the following: GPL GLA RKG (GPO)$_4$ (SEQ ID NO:15).

A "homolog" of a protein includes one or more conservative amino acid substitutions, which are selected from other members of the class to which the amino acid belongs. For example, it is well known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide.

Conservative amino acid substitutions are defined herein to result from exchange of amino acid residues from within one of the following classes of residues: Class I: Ala, Gly, Ser, Thr, and Pro (representing small aliphatic side chains and hydroxyl group side chains); Class II: Cys, Ser, Thr, and Tyr (representing side chains including an —OH or —SH group); Class III: Glu, Asp, Asn, and Gln (carboxyl group containing side chains): Class IV: His, Arg, and Lys (representing basic side chains); Class V: Ile, Val, Leu, Phe, and Met (representing hydrophobic side chains); and Class VI: Phe, Trp, Tyr, and His (representing aromatic side chains). The classes also include related amino acids such as 3-Hydroxyproline and 4-Hydroxyproline in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

Homologs, as that term is used herein, also include modified proteins. Modifications of proteins include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

In those aspects where the trigger protein forms a triple helical conformation, the triple helical conformation may be stabilized by the use of an organic scaffold (see, for instance, Goodman et al., *Biopolymers (Peptide Science)*, 1998, 47, 127-142; Jefferson et al., *J. Am. Chem. Soc.*, 1998, 120, 7420-7428; and Kwak et al., *J. Am. Chem. Soc.*, 2002, 124, 14085-14091), transition metal ions (see, for instance, Melacini et al., *J. Am. Chem. Soc.*, 1996, 118, 10359-10364; and Melacini et al, *J. Am. Chem. Soc.*, 1996, 118, 10725-10732), and peptide amphiphiles such a Cys-knot (see, for instance, Muller et al., *Biochemistry*, 2000, 39, 5111-5116; Ottl et al., *FEBS Lett*, 1996, 398, 31-36; and Ottl et al., *Tetrahedron Lett.*, 1999, 40, 1487-90) and a Lys-knot (see, for instance, Heidemann et al., *Adv. Polym. Sci.*, 1982, 43, 143-203; Fields et al., *Biopolymers*, 1993, 33, 1695-1707; and Grab et al., *J. Biol. Chem.*, 1996, 271(21), 12234-12240).

One, two, or three trigger proteins are covalently attached to a lipoprotein. Methods for the covalent attachment of two molecules are routine in the art and include, for instance, the use of an amide, ester, or ether bond, streptavidin and biotin (see, for instance, Bally (U.S. Pat. No. 5,171,578)), and activation of a polypeptide with carbodiimide followed by coupling to the activated carboxyl groups (Neurath (U.S. Pat. No. 5,204,096)). Other examples of methods that can be used to covalently bind a protein to a lipid are disclosed in Konigsberg et al. (U.S. Pat. No. 5,258,499). In one embodiment, the lipoprotein may be present in a nanoparticle at a concentration of at least 10 mol % to no greater than 60 mol %. In one embodiment, the lipoprotein is present in a nanoparticle at a concentration of at least 10 mol %, at least 20 mol %, at least 30 mol %, at least 40 mol %, or at least 50 mol %. In one embodiment, the lipoprotein is present in a nanoparticle at a concentration of no greater than 60 mole percent (mol %), no greater than 50 mol %, no greater than 40 mol %, no greater than 30 mol %, or no greater than 20 mol %.

Optionally, a spacer group is present between the lipid and the trigger protein. A spacer group is nearly any structure that is present between the saturated lipid and the trigger protein, and acts to move the trigger protein further from the surface of the nanoparticle. Many useful spacer groups are commercially available from, for instance, Sigma Aldrich. Generally, a spacer group is hydrophilic, and it can be neutral. Two examples of spacer regions that are useful herein have the following structure: —CONH—(CH$_2$CH$_2$O)$_{n'}$—, —(CH$_2$)$_{n''}$—NHCO—(CH$_2$)$_{n'''}$—, where n is 1 to 6, and n', n'', and n''' are each independently at least 2. A preferred example of a spacer region has the following structure: —CONH—(CH$_2$CH$_2$O)$_2$—(CH$_2$)$_2$—NHCO—CH$_2$—.

In one embodiment, a nanoparticle also includes a membrane stabilizer. Examples of compounds that may be used as membrane stabilizers include, but are not limited to, essentially any synthetic salt of cholesterol or amphiphilic cholesterol, such as cholesterol hemisuccinate. In one embodiment, the membrane stabilizer may be present in a nanoparticle at a concentration of at least 1 mol % to no greater than 30 mol %. In one embodiment, a membrane stabilizer is present in a nanoparticle at a concentration of at least 1 mole percent (mol %), at least 3 mol %, at least 5 mol %, at least 7 mol %, at least 10 mol %, or at least 20 mol %. In one embodiment, a membrane stabilizer is present in a nanoparticle at a concentration of no greater than 30 mole percent (mol %), no greater than 20 mol %, no greater than 10 mol %, no greater than 7 mol %, no greater than 5 mol %, or no greater than 3 mol %.

In some aspects, a nanoparticle is echogenic. Echogenic nanoparticles provide both imaging properties and rapid release of the encapsulated cargo. Advantageously, the nanoparticles have the ability to both image drug delivery and treat disease. An echogenic nanoparticle includes an echogenic molecule. Echogenicity is the ability to bounce an echo (e.g. return the signal) in, for example, ultrasound imaging. In some embodiments, the echogenic molecule may be incorporated into a bilayer membrane of a nanoparticle. In other embodiments, the echogenic molecule may be encapsulated in the interior compartment. In some embodiments, the echogenic molecule includes air (about 78% nitrogen, about 21% oxygen, and about 1% argon, carbon dioxide, and other trace gases), but other gases may be used.

The nanoparticles described herein typically have a spherical structure that encapsulates an interior compartment. This interior compartment includes a liquid that is aqueous or non-aqueous. The compartment may also include one or more compounds present in the liquid. The compound may be, for instance, a liquid, a solid that is dissolved in the liquid, or a solid that is suspended in the liquid. A compound may be, for example, an organic compound, an inorganic compound, a metal ion, a polypeptide, a non-ribosomal polypeptide, a polyketide, a peptidomimetic, or a polynucleotide. Examples of compounds include, for instance, polynucleotides such as DNA plasmids, imaging agents such as positive or negative contrast agents (e.g., gadolinium or magnetic particles), fluorescent dyes (e.g., carboxyfluorescein), dyes (e.g., calcein dye), radio imaging agents, quantum dots, chemoattractants, and therapeutic agents, such as chemotherapeutic agents and enzyme inhibitors. For instance, a therapeutic agent may be an angiogenesis inhibitor, such as those marketed under the tradenames sorafenib, sunitinib, or cabozantinib. A compound may be therapeutic (i.e., able to treat or prevent a disease) or non-therapeutic (i.e., not directed to the treatment or prevention of a disease). The liquid may include a pharmaceutically acceptable carrier. "Pharmaceutically acceptable" refers to a diluent, carrier, excipient, salt, etc., that is compatible with the other compounds present in the compartment, and not deleterious to a recipient thereof. The compartment may include a compound that inhibits the activity of the protease that cleaves the trigger protein present on the surface of the nanoparticle. In those aspects where the trigger protein present on the surface of the nanoparticle is cleaved by gelatinase-A and/or gelatinase-B, an inhibitor of gelatinase-A and/or gelatinase-B activity may be used. Examples of gelatinase-A and gelatinase-B inhibitors are known. An example of such a compound is H-Cys$^1$-Thr-Thr-His-Trp-Gly-Phe-Thr-Leu-Cys$^{10}$-OH (cyclic: 1→10). In those aspects where the trigger protein present on the surface of the nanoparticle is cleaved by ADAM10, an inhibitor of ADAM10 activity may be used. Examples of ADAM 10 inhibitors are known. Examples of such compounds include GI254023X and INCB7839.

A nanoparticle described herein has the activity of maintaining the disulfide bond of the lipid-S—S-PEG molecule under certain conditions and breaking the disulfide bond under other conditions. The PEG groups shield the substrate lipopeptides from hydrolysis in the presence of certain levels of a reducing agent, such as glutathione. However, in the presence of elevated levels of a reducing agent, the PEG groups are reductively removed, exposing the lipopeptides. The resultant hydrolysis of a peptide bond of a trigger protein by an enzyme, such as MMP-9 or ADAM10 disturbs the liposomal lipid bilayer, leading to the release of contents of the compartment. In vivo, the PEG groups shield the substrate lipopeptides from hydrolysis in circulation, and thus are stable in physiological conditions and in conditions prevalent in the circulatory system, such as in human serum. However, in the presence of the higher reducing agent levels prevalent in the extracellular matrix of some tissues, such as tumor tissue, the PEG groups are reductively removed.

Whether a nanoparticle is stable under the appropriate conditions and releases its cargo under the appropriate conditions can be determined when incubated as described in the Example. Briefly, 200 µL, of nanovesicles, 160 µL, of HEPES buffer (pH 8) with added $Ca^{2+}$ and $Zn^{2+}$ ions (10 mM, osmolarity adjusted to 290 with NaCl) are incubated in either 10% human serum or the combination of protease (e.g., MMP-9 at 2 µM or ADAM10 at 1000 nM) and glutathione (50 µM). A nanoparticle useful in the methods described herein will be stable in conditions that mimic those present in the circulatory system, such as 10% human serum, and not stable (e.g., it will release its contents) in the presence conditions that mimic those present in a tumor microenvironment. An example of tumor microenvironment-like conditions include a protease (e.g., MMP-9 or ADAM10) and glutathione, The ratios of first lipid, second lipid, lipoprotein, and membrane stabilizer can be varied in a nanoparticle. In one embodiment, mol % of the second lipid:lipoprotein:first lipid:membrane stabilizer is 60:30:5:5. In other embodiments, a change in the mol % of lipoprotein, first lipid, and/or membrane stabilizer can be compensated by changing the mol % of the second lipid.

Methods of Making Nanoparticles

Also provided herein are methods of making the nanoparticles described herein. Methods for preparing liposomes are also known in the art and include, for example, sonication and extrusion. In some embodiments, liposomes are prepared using methods which produce a narrow size distribution. Suitable lipids (as described elsewhere herein) are dissolved in a suitable organic solvent and mixed. The lipid mixture is dried to form a lipid dry film. In some embodiments, the drying conditions include air drying, freeze drying, vacuum drying, or any combination thereof. The lipid dry film is rehydrated in a suitable aqueous solvent and subjected to conditions effective for liposomes to form. In some embodiments, the conditions include sonication. Prepared liposomes may be isolated from the solution by any suitable means including, for example, extrusion.

To incorporate the echogenic compound, nanoparticles are subjected to freeze-thaw and lyophilisation processes. Freeze-thaw and lyophilisation (e.g., freeze-drying) processes create defects in the bilayer membrane. In some embodiments, the freeze-thaw and lyophilisation processes are done in the presence of a cryoprotectant. The presence of the cryoprotectant provides protection for the bilayer membrane and prevents the induction of defects. In some embodiments, the cryoprotectant is a weak cryoprotectant and cannot provide adequate protection for the bilayer, thus allowing minor defects in the bilayer membrane. The minor defects allow the echogenic compound (e.g., air) to enter the bilayer curing reconstitution of the lyophilized powder in a buffer solution. Suitable weak cryoprotectants include, for example, mannitol, trehalose, and the like. In some embodiments, the cryoprotectant includes mannitol. In some embodiments, the mannitol is present in a concentration of 100 mM to 700 mM. For example, mannitol may be present in a concentration of at least 100 mM, at least 200 mM, at least 300 mM, or at least 400 mM. For example, mannitol may be present in a concentration of no greater than 500 mM, no greater than 400 mM. In one embodiment, mannitol is present in a concentration of 320 mM.

In embodiments where a cargo is encapsulated in the compartment of the nanoparticle, the cargo may be loaded into the nanoparticle by passive loading or by active loading. Passive loading may include, for example, thin-film hydration-sonication and solvent-exchange methods as described in Lee et al. (2012 *J Control Release* 161:473-83). A thin-film hydration-sonication and solvent-exchange method includes dissolving suitable polymers in an aqueous solvent, dissolving the cargo in a solvent, combining the cargo solution with the polymer solution, and allowing the polymerization reaction which forms nanoparticles to also incorporate the cargo.

Active loading may include, for example, a pH gradient method as described in Mayer et al. (1990 *Biochimica et*

*Biophysica Acta (BBA)—Biomembranes* 1025:143-51). Briefly, a pH gradient method includes preparing the nanoparticles ecapsulating an acidic buffer, neutralizing the external pH, dissolving the cargo in a solvent, and incubating the cargo in solution with the nanoparticles to stimulate the nanoparticles to incorporate the cargo. Unencapsulated drugs can be removed, for example, by passing the nanoparticles through a size exclusion column.

Compositions

Also provided herein are compositions including a nanoparticle. Such compositions typically include a pharmaceutically acceptable carrier. Additional active compounds can also be incorporated into the compositions.

A composition may be prepared by methods well known in the art of pharmacy. In general, a composition can be formulated to be compatible with its intended route of administration. Examples of routes of administration include perfusion and parenteral, e.g., intravenous, intradermal, subcutaneous, oral (e.g., inhalation), transdermal (topical), transmucosal, and rectal administration. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. The pH can be adjusted with acids or bases, such as hydrochloric acid or sodium hydroxide. A composition can be enclosed in ampoules, disposable syringes or multiple dose vials.

Compositions can include sterile aqueous solutions or dispersions and sterile powders for the extemporaneous preparation of sterile solutions or dispersions. For intravenous administration, suitable carriers include, for instance, physiological saline, bacteriostatic water, or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (a nanoparticle described herein) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent, an edible carrier, or the combination. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can also be prepared in the form of suppositories (e.g., with conventional suppository bases such as cocoa butter and other glycerides) or retention enemas for rectal delivery.

The active compounds may be prepared with carriers that will protect the nanoparticle against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc.

The concentration of nanoparticles in a composition, e.g., from less than 0.05%, usually at or at least 2-5% to as much as 10 to 30% by weight and will be selected primarily by fluid volumes, viscosities, etc., in accordance with the particular mode of administration selected. Toxicity and therapeutic efficacy of nanoparticles containing a therapeutic agent can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the methods described herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a composition containing a nanoparticle can include a single treatment or a series of treatments.

Methods of Use

Further provided are methods for using the nanoparticle described herein. In one aspect, the methods include exposing a cell to a compound present in a nanoparticle. Exposing a cell may include delivery of an agent to the extracellular region of a tissue. The agent may be, for instance, a non-therapeutic agent such as an imaging agent, or a therapeutic agent such as a chemotherapeutic agent. The tissue may be one with elevated levels of a reducing agent, such as the extracellular matrix present in a tumor.

In another aspect, the method includes treating certain diseases in a subject. The subject is a mammal, preferably a human. As used herein, the term "disease" refers to any deviation from or interruption of the normal structure or function of a part, organ, or system, or combination thereof, of a subject that is manifested by a characteristic symptom or set of symptoms. Diseases include cancers such as, for instance, breast cancer, colorectal cancer, lung cancer, prostate cancer, pancreatic cancer, ovarian cancer, and melanoma. Other diseases include, for instance, gouty arthritis, inflammatory bowel disease (ulcerative colitis), abdominal aortic aneurysms, quiescent Crohn's Disease, glaucoma, sunlight induced premature skin aging, atherosclerotic plaques, breach of blood-brain barrier after a stroke, arthritis, and deep wounds. Typically, whether a subject has a disease, and whether a subject is responding to treatment, is determined by evaluation of symptoms and/or signs associated with the disease. As used herein, the term "symptom" refers to objective evidence of disease present in a subject. As used herein, the term "clinical sign" or, simply, "sign" refers to objective evidence of disease caused by disease. Symptoms and/or signs associated with diseases referred to herein and the evaluation of such symptoms and/or signs are routine and known in the art. Examples of symptoms of cancers include, for instance, the presence and size of tumors and metastatic tumors (i.e., tumors formed by tumor cells from a primary tumor), and the presence and amount of biomarkers. Biomarkers are compounds, typically polypeptides, present in a subject and indicative of the progression of cancer. Biomarkers for many cancers are known, including biomarkers that are indicative of pancreatic cancer (Misek et al., 2007, J. Natl. Compr. Canc Netw., 5(10):1034-1041)

Treatment of a disease can be prophylactic or, alternatively, can be initiated after the development of a disease. Treatment that is prophylactic, for instance, initiated before a subject manifests symptoms of a disease, is referred to herein as treatment of a subject that is "at risk" of developing a disease. An example of a subject that is at risk of developing a disease is a person having a risk factor, such as a genetic marker, that is associated with the disease. Examples of genetic markers indicating a subject has a predisposition to develop certain cancers such as breast, prostate, or colon cancer include alterations in the BRAC1 and/or BRAC2 genes. Another example of a subject at risk of developing a disease is a person having a tumor containing metastatic cells, where such a person is at risk of developing metastatic tumors. Treatment can be performed before, during, or after the occurrence of the diseases described herein. Treatment initiated after the development of a disease may result in decreasing the severity of the symptoms of one of the conditions, or completely removing the symptoms.

The methods typically include administering to a subject at risk of developing a disease or having the disease a composition including an effective amount of a nanoparticle, wherein a symptom associated with the disease is decreased. As used herein, an "effective amount" of a composition described herein is the amount able to elicit the desired response in the recipient. Whether a nanoparticle is expected to function in the methods described herein can be evaluated using ex vivo models and animal models. Such models are known in the art and are generally accepted as representative of disease or methods of treating humans. Examples of ex vivo models include two dimensional cell culture and three dimensional tumor like cell culture. Examples of cells that can be used in such models are known to the person skilled in the art. In embodiments where the disease is pancreatic cancer, non-limiting examples of cells include pancreatic ductal carcinoma cells such as PANC-1 and MIAPaCa-2). Examples of in vivo models include the nude mouse model, where human tumor cells are injected into the animal. Such ex vivo and in vivo models are commonly accepted as a general model useful for the study of a wide variety of cancers.

Also provided is a kit for practicing the methods described herein. The kit includes one or more of the nanoparticles in a suitable packaging material in an amount sufficient for at least one administration. Optionally, other reagents such as buffers and solutions are also included. Instructions for use of the packaged nanoparticle(s) are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the nanoparticle(s) can be used for the methods described herein. In addition, the packaging material contains instructions indicating how the materials within the kit are employed to practice the methods. As used herein, the term "package" refers to a solid matrix or material such as glass, plastic, paper, foil, and the like, capable of holding within fixed limits the nanoparticle(s). Thus, for example, a package can be a glass vial used to contain appropriate quantities of the nanoparticle(s). "Instructions for use" typically include a tangible expression describing the conditions for use of the nanoparticle(s).

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The present invention is illustrated by the following examples. It is to be understood that the particular examples, materials, amounts, and procedures are to be interpreted broadly in accordance with the scope and spirit of the invention as set forth herein.

Example 1

Significant differences in biochemical parameters between normal and tumor tissues offer an opportunity to chemically design drug carriers which respond to these changes and deliver the drugs at the desired site. For example, overexpression of the matrix metalloproteinase-9 (MMP-9) enzyme in the extracellular matrix of tumor tissues can act as a trigger to chemically modulate the drug delivery from the carriers. In this study, an MMP-9-cleavable, collagen mimetic lipopeptide was synthesized which forms nano-sized vesicles with the POPC, POPE-SS-PEG and cholesteryl-hemisuccinate lipids. The lipopeptide retains the triple-helical conformation when incorporated into these nanovesicles. The PEG groups shield the substrate lipopeptides from hydrolysis by MMP-9. However, in the presence of elevated glutathione levels, the PEG groups are reductively removed, exposing the lipopeptides to MMP-9. The resultant peptide-bond cleavage disturbs the vesicles' lipid bilayer, leading to the release of encapsulated contents. These PEGylated nanovesicles are capable of encapsulating the anticancer drug gemcitabine with 50% efficiency. They were stable in physiological conditions and in human serum. Effective drug release was demonstrated using the pancreatic ductal carcinoma cells (PANC-1 and MIAPaCa-2) in two-dimensional and three-dimensional "tumor-like" spheroid cultures. A reduction in tumor growth was observed after intravenous administration of the gemcitabine-encapsulated nanovesicles in the xenograft model of athymic, female nude mice.

Materials and Methods

The POPS—S—S-PEG disulfide lipid was synthesized as shown in FIG. 1.

Synthesis and Characterization of Lipopeptide

The lipopeptide LP [$CH_3(CH_2)_{16}CONH$-GPQGIAGQR(GPO)$_4$GG-COOH] was synthesized by employing microwave assisted solid phase peptide synthesizer (Liberty, CEM Corporation, Matthews, S.C.) by following the protocol previously established in our laboratory (Pompella et al., *Biochem pharm* 2003, 66 (8), 1499-1503). The lipopeptide was purified by reverse phase HPLC (Shimadzu Scientific Instruments) using a diphenyl semi-preparatory column (Grace Vydac, 300 Å pore diameter silica, 5 µm particle size, 10 mm×250 mm) as the stationary phase. A linear gradient (0-70%) of acetonitrile (with 0.1% trifluoroacetic acid) in water (with 0.1% trifluoroacetic acid) was used at a flow rate of 8 mL/min over 60 min. The chromatogram was recorded at 235 nm using a UV detector. After freeze drying the eluents, the peptide was characterized employing MALDI-TOF mass spectrometry with an AB 4800 MALDI TOF/TOF mass analyzer. An observed mass of 2332.3 Da in MALDI spectra confirmed the LP (calculated mass: 2332.2 Da). The collagen mimetic triple helical structure of the lipopeptide was assessed by CD spectrometry employing a Jasco J-815 CD spectrometer with a quartz cuvette of 1 mm path length. The positive peak at 222 nm and the negative peak at 198 nm confirmed the triple helical structure of collagen mimetic peptide.20 For the CD spectroscopic studies, 32 accumulations were recorded for each spectra.

Synthesis of POPE-SPDP Derivative

To a stirred solution of POPE (100 mg, 0.139 mmol) in dichloromethane (10 mL), diisopropylethyl amine (33 µL, 0.167 mmol) was added followed by SPDP—OSu (46 mg, 0.1462 mmol). Upon stirring overnight under an inert atmosphere, the reaction mixture was washed with water, dried over Na2SO4 and the solvent was evaporated under reduced pressure. The residue was subjected to flash chromatography (Rf=0.7 in 15% MeOH in CH2Cl2) to afford pure product as a waxy white solid (104 mg, 82%).

1H NMR (CDCl3,400 MHz): δ 0.81-0.89 (m, 6H), 1.2-1.4 (m, 41H), 1.6 (br s, 4H), 1.95-2.05 (q, 4H), 2.25-2.35 (m, 4H), 2.6-2.8 (m, 6H), 3.0-3.1 (m, 2H), 3.41 (s, 2H), 3.8-3.95 (m, 4H), 4.3-4.4 (m, 2H), 5.2 (s, 1H), 5.3-5.4 (m, 2H), 7.12-7.2 (t, 1H), 7.68-7.8 (m, 2H), 8.4 (d, 2H).

Synthesis of POPE-S—S-PEG

Figure 11:
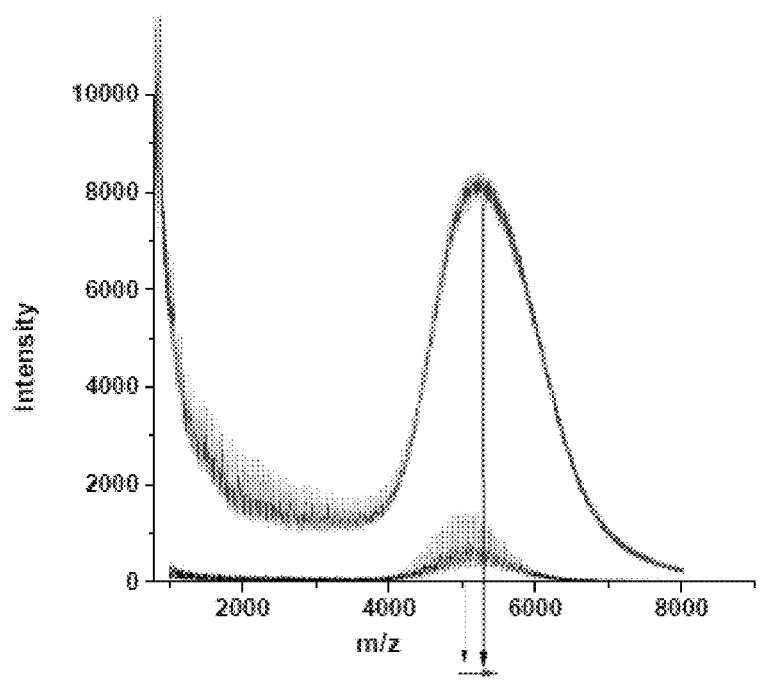
FIG. 11. MALDI spectra confirming POPE-SS-PEG5000 synthesis. Overlay plot of MALDI spectra indicating increase in mass of PEG5000 (lower trace) after successful synthesis of POPE-SS-PEG5000 (upper trace).

The product obtained in the previous reaction (35 mg, 0.038 mmol) was reacted with PEG-SH (MW: 5000, 191 mg, 0.038 mmol) in dichloromethane (8 mL) under inert condition for 12 h. The volume of the reaction mixture was reduced under reduced pressure and then subjected to PLC ($R_f$=0.8 in 15% MeOH in CH2Cl2). The pure product was isolated as a white waxy solid (125 mg, 56%). 1H NMR (CDCl3, 400 MHz): δ 0.81-0.89 (m, 6H), 1.19-1.42 (m, 45H), 1.51-1.62 (m, 4H), 1.95-2.05 (q, 4H), 2.24-2.32 (m, 4H), 2.57-2.67 (m, 2H), 2.85-2.9 (t, 1H), 2.91-2.96 (t, 1H), 3.01-3.09 (m, 2H), 3.4-3.5 (m, 2H),3.52-3.75 (m, 307H)3.8-3.86 (m, 2H), 3.86-4.0 (m, 4H), 4.1-4.2 (m, 1H), 4.32-4.4 (m, 1H), 5.15-5.25 (s, 1H), 5.3-5.4 (m, 2H). 13C NMR (CDCl3, 100 MHz): δ 13.90, 14.31, 19.27, 22.87, 25.06, 27.43, 29.51, 29.56, 29.87, 29.93, 32.10, 34.3, 59.22, 70.75, 72.13, 129.87, 130.168. MALDI mass spectra also confirmed the conjugation of PEG (FIG. 11).

Preparation of Carboxyfluorescein Encapsulated Nanovesicles

The nanovesicles (liposomes) were prepared by mixing POPC lipid (Avanti Polar Lipids), synthesized lipopeptide LP, POPE-SS-PEG5000 and cholesteryl hemisuccinate in molar proportions of 60:30:5:5, respectively. All the lipids were dissolved in chloroform. The chloroform was removed using a rotary evaporator to form a thin lipid film in a round-bottom flask. The film was further vacuum dried overnight inside a desiccator. The film was then hydrated at 60° C. for 2 hours with 100 mM carboxyfluorescein solution prepared in HEPES buffer (pH 7.4). The formed vesicles were subjected to ultrasonication for 45 minutes using an Aquasonic bath sonicator (Model: 250D, power level 9). The resulting vesicles were then extruded through 0.8 μm and, subsequently, 0.2 μm filters to obtain vesicles with a uniform size. To remove the unencapsulated dye, the vesicles were passed through a Sephadex G50-size exclusion column, and an orange band of carboxyfluorescein-encapsulated nanovesicles was collected. These vesicles were used for the release and imaging experiments.

Preparation of Gemcitabine-Encapsulated Nanovesicles

Gemcitabine was encapsulated in the nanovesicles with the pH gradient method (Celano et al., BMC cancer 2004, 4 (1), 63). Nanovesicles of lipid composition POPC (Avanti Polar Lipids), LP, POPE-SS-PEG, cholesteryl hemisuccinate and lissamine rhodamine lipid (Avanti Polar Lipids) were prepared by dissolving them in chloroform in the molar proportions of 59:30:5:5:1, respectively. Chloroform was then evaporated under reduced pressure, and the resulting thin film of lipids was dried under a vacuum desiccator. This film was hydrated with 2 mL of 20-mM citric-acid buffer (pH 4). The resulting vesicles were subjected to ultrasonication for 45 minutes (at power level 9) and were then extruded through a 0.2-μm filter. Nanovesicles were collected after passing them through a Sephadex G50 gel-filtration column. These eluted nanovesicles (pH 7.4) were incubated with 1 mg/mL aqueous solution of gemcitabine at 60° C. for 2 hours. The gemcitabine solution was added to the nanovesicles to create a lipid-drug ratio of 10:1. Drug-carrying nanovesicles were again passed through the Sephadex G50 column to remove non-encapsulated gemcitabine. Entrapment efficiency of the nanovesicle was then calculated. These nanovesicles were used for cytotoxicity studies.

Calculation for Percent Entrapment of Gemcitabine

To calculate percent drug entrapment, absorbance of liposomes was measured at 268 nm (λmax of gemcitabine) before passing through Sephadex column (A1) and after collecting the eluent (A2). Dilution factor (d) was taken into consideration while calculating percent entrapment of the drug.

$$\text{Percent Entrapment} = \frac{A1 - A2d}{A1} \times 100$$

Calculation for Amount of Gemcitabine Entrapped in Nanovesicles

Gemcitabine was loaded in nanovesicles by pH gradient method. Citrate buffer (pH 4) encapsulated nanovesicles were incubated with gemcitabine, maintaining lipid:drug ration of 9:1. Example: 1 mg lipid containing vesicles were incubated with 0.1 mg of gemcitabine. Percent drug entrapment was calculated by using equation given in SC1. Percent entrapment of 50% indicated that 50 μg of gemcitabine is encapsulated in nanovesicles containing 1 mg equivalent of lipid.

Size and Morphology Analysis

The hydrodynamic diameters of the vesicles were measured using a Dynamic Light Scattering (DLS) instrument (Malvern Zetasizer Nano-ZS90). Measurements were conducted at a scattering angle of 90° using a polystyrene, latex disposable cuvette. An equilibration time of 120 seconds was kept constant for all measurements. For each sample, 6 readings were recorded averaging 6 runs for the same sample. In order to observe size changes in the presence of added MMP-9 and GSH, the nanovesicles that encapsulated gemcitabine were incubated with MMP-9 and GSH. Size changes were monitored for 24 hours with DLS, and the morphology change was observed using an atomic force microscope (AFM). For AFM imaging, the nanovesicles were deposited on a mica sheet and were imaged using Multimode™ atomic force microscope with a Nanoscope IIIa controller and a J-type piezo scanner (Veeco Metrology Group, Santa Barbara, Calif.). An antimony (n) doped Si tip was used for obtaining images in the Tapping Mode.

Release Studies

Figure 12:
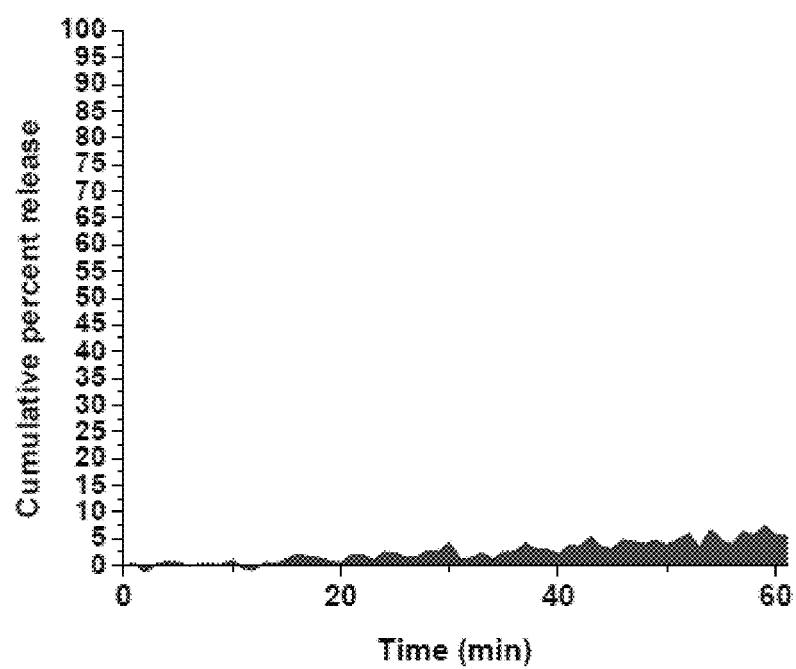
FIG. 12. Release profile of carboxyfluorescein encapsulated nanovesicles in human serum. Cumulative percent release of carboxyfluorescein from nanovesicles was observed to be less than 5 (shaded area) in 60 min in the presence of 10% human serum which was suggestive of stability of nanovesicles in circulation.

The release of the encapsulated dye was monitored with a fluorescence spectrophofluorimeter (Spectramax-M5, Molecular Devices, Inc.). Carboxyfluorescein (100 mM) was encapsulated in liposomes, and the release was monitored as function of time (excitation: 480 nm; emission: 515 nm). Release from the nanovesicles was recorded for 60 minutes in 30-second intervals. The experiments were carried out in a 96-well plate (6 repeats for each measurement). Each well contained 20 μL of nanovesicles and 160 μL of HEPES buffer (pH 8) with added Ca2+ and Zn2+ ions (10 mM, osmolarity adjusted to 290 with NaCl). Contents released in response to added recombinant MMP-9 (2 μM) and GSH (50 μM) were monitored for 60 minutes. Release in human serum (10%) was also monitored for 60 minutes (FIG. 12). After 60 minutes, Triton-X100 was added to each well to disrupt the nanovesicles, and emission intensity was measured. This intensity was considered to be for complete release of the encapsulated dye, and the percentage released for each experiment was calculated using the following formula:

$$\text{PERCENT RELEASE} = \frac{\text{Observed intensity after 60 min} - \text{Emission intensity after triton treatment} -}{\text{Emission intensity after triton treatment} - \text{Initial intensity before treatment}} \times 100$$

Cell Culture

Pancreatic-cancer cell lines PANC-1 and MIAPaCa-2 were obtained from American Type Culture Collection (Manassas, Va.). PANC-1 cells were cultured in RPMI media (without phenol red) that were supplemented with 2% antibiotics (penicillin, streptomycin) and 10% v/v fetal bovine serum. The MIAPaCa-2 cells were cultured in DMEM media that were supplemented with 2% horse serum and 2% antibiotics. All cell lines were grown at 37° C. in a humidified atmosphere containing 5% $CO_2$.

Alamar Blue Assay with a Monolayer Cell Culture

Figure 15:
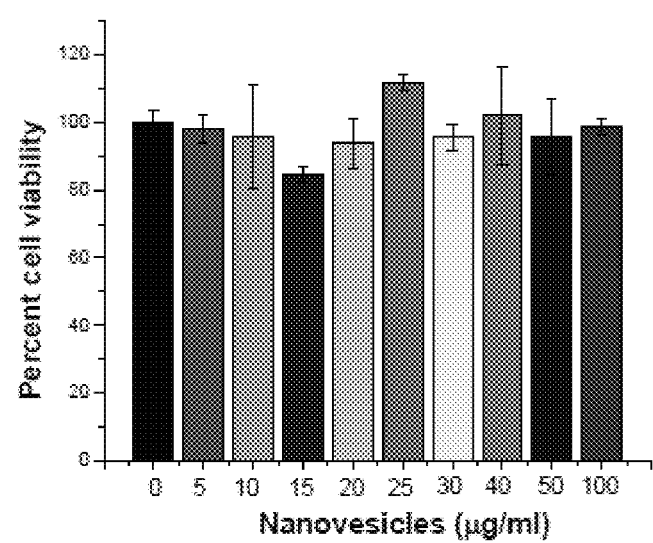
FIG. 15. Toxicity of nanovesicles. Nanovesicles did not show any toxicity when incubated with MIAPaCa-2 cells for 72 hours.

Cytotoxicity of the encapsulated gemcitabine was measured by treating the PANC-1 and MIAPaCa-2 cells with nanovesicles. The cells were incubated (1,000 per well) in a 96-well plate after trypsinizing the flask and making a cell suspension. RPMI media (100 μL) were added to each well. Cells were allowed to grow for one doubling time. The plate was divided into three groups: control, gemcitabine treated and gemcitabine-encapsulated nanovesicles treated. Six replicates were recorded for each sample. The control group did not receive any treatment. Gemcitabine-treated cells received 10 μM of gemcitabine, and nanovesicle-treated cells received an equivalent amount of encapsulated gemcitabine. The treatment was carried out for 3 days, and cell toxicity was recorded after 72 hours with the Alamar Blue assay by following the supplier's (Life Technologies) protocol. Alamar Blue solution (10 µL) was added to all the wells and incubated for 2 hours, and the absorbance was recorded at 585 nm for cytotoxicity calculation (FIG. 15).

Estimation of Cell-Secreted MMP-9 Concentration

Conditioned media from confluent cultures of PANC-1 and MIAPaCa-2 cells were collected, and a concentration of secreted MMP-9 was estimated by using a commercially available MMP-9 ELISA kit (RayBio Tech). The manufacturer's instructions were followed to estimate the MMP-9 secreted by the cells.

Three-Dimensional Spheroid Cell Culture

Based on the ELISA results, the PANC-1 cell line was selected for the spheroid culture because it showed the highest levels of secreted MMP-9. In order to prepare the cell spheroids, agar molds, each having the capability to form 96 spheroids of uniform size, were created. To prepare the plates, a slightly modified protocol provided by Microtissues™ (http://www.microtissues.com/3dcellculture_protocols/Casting_Equilibrating_and_Seeding_the_3D_Petri_Dish.pdf) was used. The prepared plates were equilibrated with RPMI media for 1 hour at 37° C. and placed in 6-well plates, and 2 mL of RPMI media were added to each well to provide nutrition for the cells seeded in the plates. Agar plates were then seeded with 75 µL of cell suspension containing 10,000 cells in each plate which formed spheroids after 3 days of incubation at 37° C. These spheroids were used for cell-viability and oxidative-stress studies.

Lactate Dehydrogenase (LDH) Assay

LDH was measured using a kit supplied by G-Biosciences (Cytoscan™ LDH Cytotoxicity assay). The manufacturer's instructions were followed to measure the LDH released in response to cytotoxicity caused by the release of gemcitabine from the nanovesicles. This assay was carried out using 1-day, 3-day and 5-day old spheroids.

Alamar Blue Assay with 3-D Cell Culture

Plates containing 96 spheroids molds were prepared, and cells were allowed to grow for 5 days in order to form spheroids. These plates were divided into 3 groups on the basis of the treatment they received: control, drug treated and drug-encapsulated nanovesicles. Each group contained 6 plates with 96 spheroids. The control group received the same nutrition media as the other groups. The drug-treated group received 10 µM of gemcitabine, and the test group received drug-encapsulated nanovesicles (encapsulating 10 µM of gemcitabine). Spheroids in all groups received the treatment for 72 hours. Subsequently, all the media surrounding the micro-mold were removed. The spheroids were treated with TryPLE (Life Technologies) and were incubated for 1 hour at 37° C. to ensure dissociation of all the cells in the spheroid. RPMI media (3 mL) were added to each plate and were triturated to remove all the cells from the plate. From the cell suspension obtained, 100 µL from each plate were seeded on a new clear-bottom, 96-well plate (repeated 6 times for each well). Additional growth medium (100 µL) was added to all the wells receiving the cell suspension. The cells were allowed to grow for one doubling time, and the Alamar Blue assay was carried out per the manufacturer's protocol, as described before.

Confocal Fluorescence Microscopic Imaging

Carboxyfluorescein-encapsulated nanovesicles were used to visualize the release of contents in 7-day-old spheroids of PANC-1 cells. Nanovesicles devoid of lipopeptide LP were used as a control. The spheroids were treated in the plate with the control and sample nanovesicles by incubating for 4 hours at 37° C. The spheroids were then washed (3×) with culture media. Spheroid-holding plates were then centrifuged to dislodge spheroidsin the media. These spheroids were then imaged using a Zeiss AxioObserver Z1, inverted microscope with an LSM700 laser-scanning head attachment and a 20× 0.4 LD Plan-Neofluar objective. The first and last appearance of the fluorescence in the sample-treated spheroids was set as the scanning range. The same comparison range was selected for the control spheroids. Images were processed with Zeiss AxioVision Rev. 4.8.1 image-analysis software (Carl Zeiss, Thornwood, N.Y.).

In-Vivo Imaging

For in-vivo imaging, athymic, Nude-Foxn1 (female, 5-6 week old), nude mice were used. PANC-1 cells (3 million) were injected subcutaneously. A tumor developed 21 days after injection. Carboxyfluorescein-encapsulated (50 mM) nanovesicles (60 µL) were injected via the tail vein. Images were recorded using a reflectance imaging system (Kodak in-vivo system FX, Carestream Health, Inc., Rochester, N.Y.). The whole-body fluorescence images were acquired using the FITC channel (excited at 480 nm and recorded at 680/720 nm) after 5 seconds of exposure. Images were recorded to monitor the release of carboxyfluorescein at the tumor site 6 hours and 24 hours after injection. The images were further processed using Kodak Molecular Imaging software (version 4.0).

In-Vivo Studies

In-vivo studies were carried out using a xenograft model for athymic, Nude-Foxn1 (female, 5-6 week old), nude mice (IACUC-approved protocol number A13066). PANC-1 cells (3 million) were injected subcutaneously into the nude mice, and the cells were allowed to grow at the injected site for 15 days. After the tumors developed, mice were divided into the control, positive control and test groups (n=3 for each group). The control group received a phosphate buffer (pH 7.4, osmolarity 325 mOsm/kg), animals in positive control group received gemcitabine (10 mg/kg/week) encapsulated in PEGylated liposomes devoid of LP and the test group received a 10-mg/kg/week dose of gemcitabine-encapsulated in the deigned MMP-9 responsive PEG cleavable nanovesicles. The treatment was administered for 4 weeks via tail-vein injection. The tumor size was recorded each week, and the tumor volume was calculated using the following formula: volume=(width)$^2$×length/2. The mice's weights were recorded throughout the study, and the mice were closely monitored for any sign of toxicity.

Results and Discussion

Coating the drug carriers with a layer of polyethylene glycol or another hydrophilic polymer imparts the long-circulating property. However, efficient interactions between the drug carrier and tumor microenvironment require the removal of the protective PEG coating from the surface of the carrier at the target site (Li et al., *J control release* 2010, 145 (3), 178). In order to impart this feature to the nanovesicles, a reduction-sensitive PEGylated lipid POPE-SS-PEG5000 was synthesized (FIG. 1). The product was confirmed by NMR and MALDI mass spectral analysis. It was expected that the long PEG chains would protect the MMP-9 substrate lipopeptide LP from cleavage in the presence of low levels of MMP-9 (50-100 nM; found in the blood) and would provide long-circulating characteristics to the nanovesicles. Increased oxidative stress often results in elevated levels of glutathione (GSH) in tumor tissues (Estrela et al., *Crit Rev Clin Lab Sci* 2006, 43 (2), 143-181). The sulfhydryl group of reduced glutathione participates in the thiol-exchange (Pompella et al., *Biochem pharm* 2003, 66

(8), 1499-1503), and this reaction was expected to reduce the disulfide bonds of the POPE-SS-PEG5000 lipid. It was expected that the resultant exposure of the collagen mimetic, substrate lipopeptides to the elevated MMP-9 levels in the tumor extracellular matrix will initiate the hydrolysis of the lipopeptides, leading to destabilization of the nanovesicles.

The lipopetide LP was designed to act as a substrate for the extracellular enzyme MMP-9 (Banerjee et al., *Bioconjugate chem* 2009, 20 (7), 1332-1339). It was previously demonstrated that LP can be successfully incorporated into liposomes and that the resultant vesicles undergo "uncorking" in the presence of elevated MMP-9 levels, releasing the encapsulated contents (Sarkar et al., *Bioconjugate chem* 2008, 19 (1), 57-64). The collagen-mimetic, MMP-9, cleavable LP was synthesized by microwave-assisted, solid-phase peptide synthesis and was purified by reverse-phase HPLC. The MMP-9 cleavage site for LP is located between the amino acids Glycine and Isoleucine (Banerjee et al., *Bioconjugate chem* 2009, 20 (7), 1332-1339). The collagen-mimetic, triple-helical structural characteristic of purified LP was confirmed by CD spectroscopy, showing a positive peak at 220 nm and a negative peak at 198 nm (Nahire et al., *Molpharmaceutics* 2012, 9 (9), 2554-2564).

Figure 2:
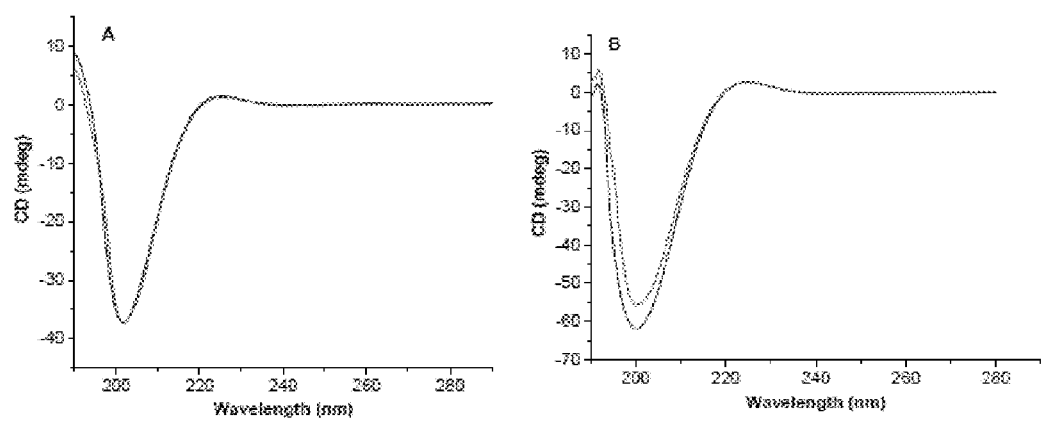
FIG. 2. CD spectra of nanovesicles (black trace) and nanovesicles treated with 50 μM of GSH (red trace) did not show any change in triple helicity (A), but treatment with MMP-9 (red trace) showed changes in the triple helicity of the nanovesicles (black trace) (B).

LP retained its triple helical structure when incorporated into nanovesicles composed of POPC (65%), POPE-SS-PEG (5%) and cholesteryl hemisuccinate (5%) (FIG. 2A, black trace). It was observed that the triple helicity of nanovesicle-incorporated LP was unchanged upon treatment with GSH (50 μM) for 1 hour (FIG. 2A). However, the triple helicity of LP was considerably reduced when incubated with 2 μM of recombinant human MMP-9 for 60 minutes (FIG. 2B).

Figure 3:
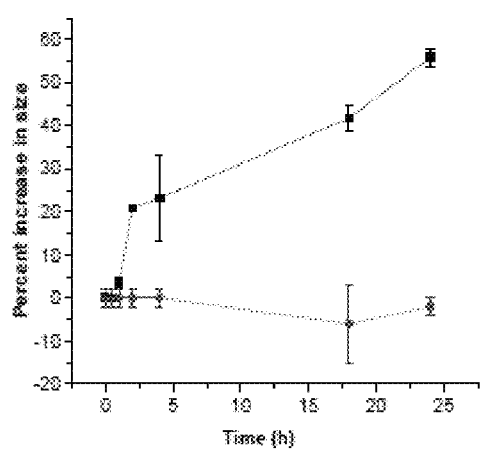
FIG. 3. Nanovesicles treated with the MMP-9 (2 μM) and GSH (50 μM) showed an increased size with time (squares, n=6). The size of the untreated nanovesicles was not affected at room temperature (circles, n=6). The straight lines connecting the observed data points are shown in the plot.
Figure 4:
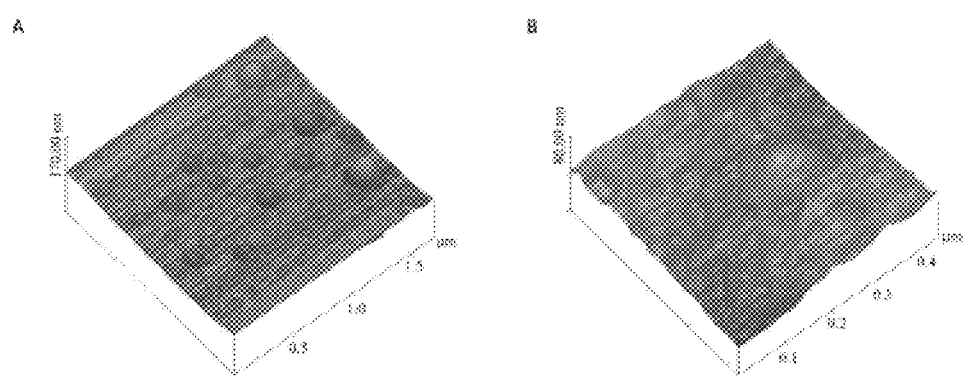
FIG. 4. AFM images for the gemcitabine-encapsulated nanovesicles (A) before and (B) after 24 hours of incubation with GSH (50 μM) and MMP-9 (2 μM).

The nanocarriers' size is relevant for passive tumor targeting because the drug carriers accumulate at the target site by infiltration through the leaky vasculature (Choi et al., *Nano lett* 2007, 7 (12), 3759-3765). The nanovesicles composed of POPC: LP: cholesteryl hemisuccinate: POPE-SS-PEG (60:30:5:5) were prepared with the freeze-drying method, followed by sonication and extrusion. The size of the prepared nanovesicles was assessed by dynamic light scattering at a 90° angle. The size of the vesicles immediately after passing through the size-exclusion column was observed to be 86 ±18 nm with a polydispersity index (PDI) of 0.3. The size of these nanovesicles was retained for 24 hours at room temperature. Treatment with MMP-9 (2 μM) and GSH (50 μM) for 24 hours increased the average size to 109±20 nm with a PDI of 0.4 (FIG. 3). This change in size upon incubation with MMP-9 indicates that the hydrolysis of the triple-helical substrate peptides by MMP-9 leads to substantial structural changes in the vesicles, resulting in the increased average diameter. The size change was also observed in the AFM imaging (FIG. 4). The observed size of the nanovesicles increased after 24 hours of treatment with MMP-9 and GSH at room temperature.

Figure 5:
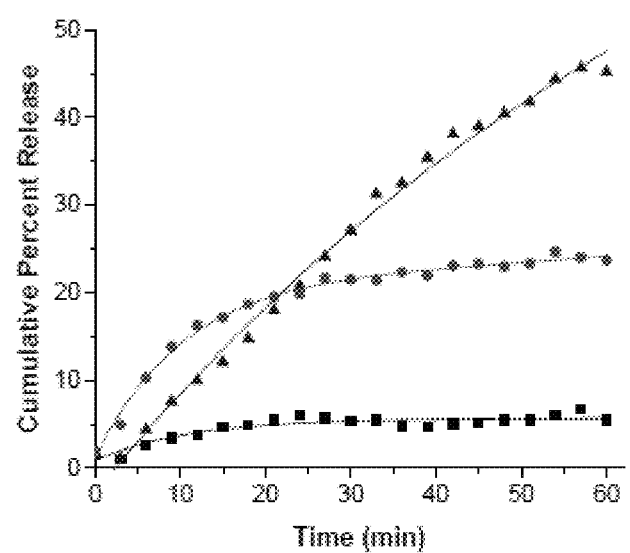
FIG. 5. Cumulative release profiles from nanovesicles under circulatory conditions (squares), in response to extracellular GSH concentration (50 μM, circles) and with an extracellular tumor mimicking the environment comprised of MMP-9 (2 μM, squares) and GSH (triangles). The traces represent the fitted curves using a single exponential-rate equation.
Figure 14:
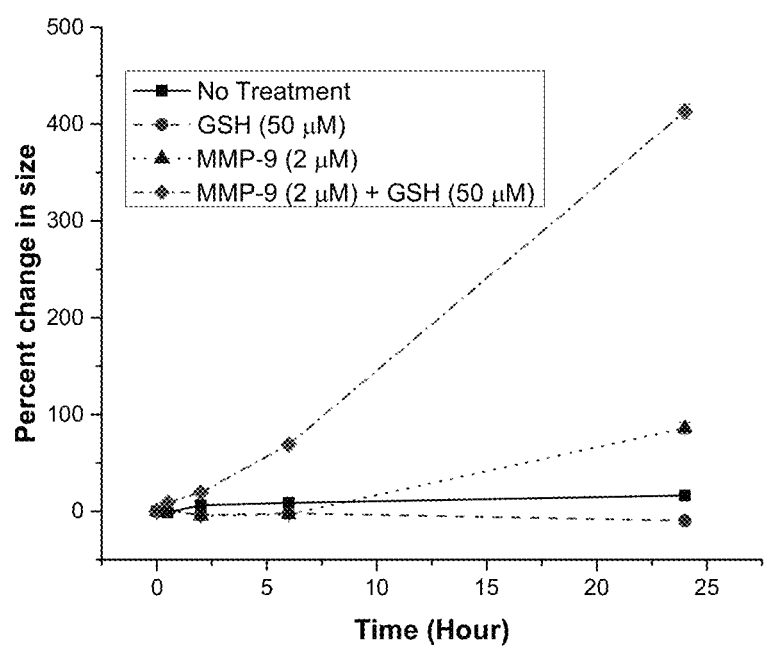
FIG. 14. Effect of MMP-9 and GSH treatments on the size of nanovesicles at 37° C. Nanovesicles treated with MMP-9 (2 μM) and GSH (50 M) showed increase in size in 24 hours (diamonds). Nanovesicles receiving only MMP-9 (2 μM) treatment also showed increase in size within 24 hours (triangles). No substantial change in size was observed when nanovesicles received no treatment (squares). Treatment with GSH (50 μM) showed a slight decrease in size over 24 hours (circles).

For quantitative estimation of contents release from the nanocarrier carboxyfluorescein (100 mM) was encapsulated in the nanovesicles. The release was monitored as a function of time in the presence of added GSH (50 μM) and MMP-9 (2 μM). An increased release was observed with both the GSH and MMP-9 treatments. The nanovesicles exhibited about a 5% release when treated with 2-μM GSH for 1 hour (FIG. 5, black squares). However, up to 22% of the encapsulated carboxyfluorescein was released after 1 hour of exposure to 50 μM of GSH (FIG. 5, red circles). To mimic the tumor's extracellular matrix environment, the nanovesicles were exposed to elevated levels of MMP-9 (2 μM) and GSH (50 μM). In these conditions, a 45% content release in 60 minutes (FIG. 5, green triangles) was observed. These release profiles can be fitted with a single exponential-rate equation with rate constants of $(12.5\pm0.6)\times10^{-2}$ s$^{-1}$ for 2 μM of MMP-9, $(11.1\pm2.2)\times10^{-2}$ s$^{-1}$ for 2 μM of GSH and $(80.5\pm0.1)\times10^{-2}$ s$^{-1}$ in the presence of 2 μM of MMP-9 and 50 μM of GSH. Note that the rate of content release was substantially higher in the presence of MMP-9 and GSH. Stimuli responsive characteristics of these liposomes were tested at 37° C. as shown in Table 1, Table 2 and FIG. 14.

TABLE 1

Release studies at 37° C.

| Treatment | Time (min) | Percent release |
|---|---|---|
| GSH (2 μM) | 60 | 15 |
| GSH (50 μM) | 60 | 22 |
| MMP-9 (2 μM) | 60 | 43 |
| MMP-9 (2 μM) and GSH (50 μM) | 60 | 58 |

TABLE 2

Release from liposomes in spent media of cells

| Conditions media of cell line | Percent release in 1 hour |
|---|---|
| Brain endothelial cell line (Does not secret MMP-9) | 15 |
| PANC-1 | 28 |

A major challenge in designing an internal, stimuli-sensitive system is the stability of the carriers in circulation before reaching the target site. To test the stability of the prepared nanovesicles, the release of carboxyfluorescein in the presence of 10% human serum was monitored. The nanovesicles exhibited less than 5% release over a period of 1 hour in 10% human serum. The stability of nanovesicles in human serum was suggestive of the designed nanovesicles' stability in circulatory conditions.

Figure 6:
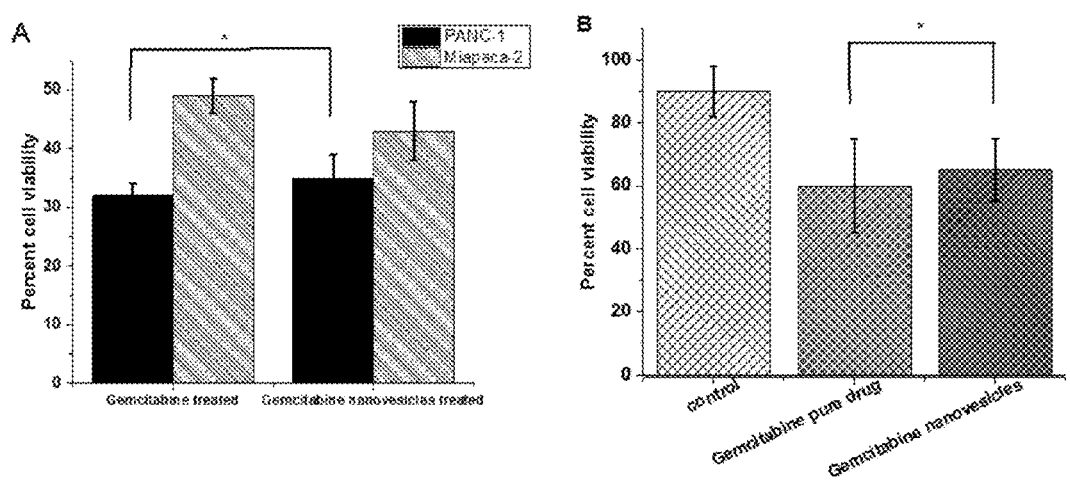
FIG. 6. Cell viability observed in the monolayer (A)(n=6) and spheroid (B) cultures (n=3) of PANC-1 and Mipaca-2 cells after gemcitabine (10 μM), gemcitabine nanovesicles (encapsulating 10 μM of gemcitabine) and control nanovesicles encapsulating PBS (20 mM, pH 7.4) treatment for 72 hours. No significant difference was observed in cell viability of PANC-1 cells in 2-D and 3-D cultures when treated with gemcitabine or gemcitabine nanovesicles (*p>0.1, **p>0.5).

Having demonstrated the release of encapsulated dye, the in-vitro and in-vivo studies were carried out using gemcitabine-encapsulated nanovesicles. Gemcitabine was encapsulated in the nanovesicles with the pH gradient method, and entrapment efficiency was observed to be 50%. These nanovesicles were used to assess cytotoxicity for the pancreatic cancer cells (PANC-1 and MIAPaCa-2) in the monolayer cultures. The cells were treated with gemcitabine and gemcitabine-encapsulated nanovesicles for 72 hours, and cell viability was measured with Alamar Blue dye. Both free and encapsulated gemcitabine showed similar toxicity for the PANC-1 (viability: 30-35%; FIG. 6, blue bars) and MIAPaCa-2 cells (viability: 45-50%; FIG. 6). The levels of secreted MMP-9 from these two cell lines was quantified by employing a commercially available ELISA kit. The results showed a higher concentration of MMP-9 in the conditioned media of PANC-1 cells (126±23 pg/mL) compared to MIAPaCa-2 cells (8±4 pg/mL). It is likely that the encapsulated gemcitabine was released from the nanovesicles by the MMP-9 secreted into the conditioned culture media. Hence, free and encapsulated gemcitabine demonstrated similar cytotoxicity, and the effect was more for the PANC-1 cells compared to the MIAPaCa-2 cells.

Figure 7:
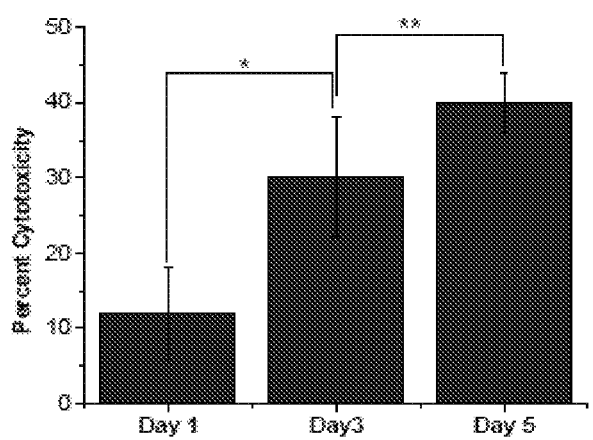
FIG. 7. LDH released in response to cell death due to the hypoxic conditions in the spheroid core after 1, 3 and 5 days. (n=6, *p<0.001, **p<0.05)

Subsequently, spheroids of uniform size were cultured by using micro-molds in each well of a 6-well microplate. After seeding the PANC-1 cells, the spheroid growth was monitored for 7 days. With the increased size, the cells in the spheroid core undergo apoptosis due to a lack of oxygen and nutrients, mimicking the hypoxic conditions observed in tumor tissues (Sutherland et al., Science 1988, 240 (4849), 177-184). This cell death in the spheroid core is reflected in increased LDH levels in the culture media (Sasaki et al., Toxicol in Vitro 1994, 8 (5), 1113-1119). A similar effect was also observed in the spheroid cultures of the PANC-1 cells (FIG. 7). Subsequently, the cytotoxicity assays were repeated with free and nanovesicle-encapsulated gemcitabine, employing the PANC-1 spheroids. It was observed that the cell viability was similar in spheroids treated with the free and encapsulated drug (FIG. 6B). It was observed that the cytotoxicity for the encapsulated gemcitabine was less in spheroids compared to the two-dimensional cultures of the PANC-1 cells.

Figure 8:
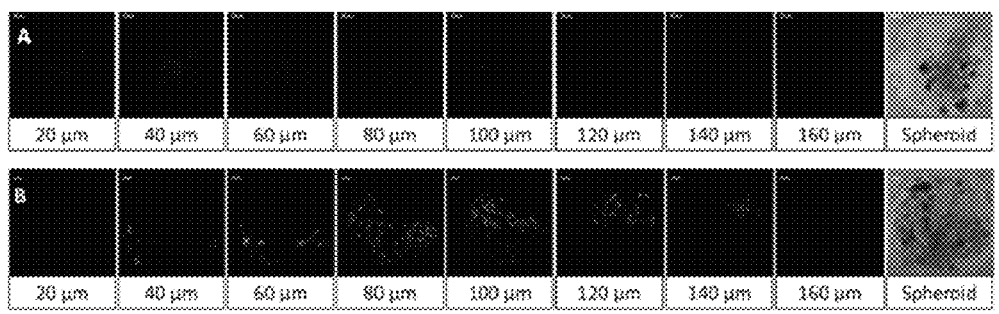
FIG. 8. Uptake of released carboxyfluorescein by the spheroids of the PANC-1 cells. Spheroids treated with MMP-9-responsive nanovesicles showed an enhanced uptake of carboxyfluorescein released from the nanovesicle (B) as compared to nanovesicles that lacked the MMP-9 responsive lipopeptide (A).

To ascertain that the encapsulated contents were released from the nanovesicles and internalized in the PANC-1 cell spheroids, the uptake was monitored with confocal fluorescence microscopy. For easier visualization, these experiments were conducted with carboxyfluorescein-encapsulated nanovesicles. Analogous liposomes were prepared without incorporating the MMP-9 substrate peptide LP and used these nanovesicles as the control. It was observed that the control nanovesicles failed to release the contents, and no significant dye internalization was detected (FIG. 8, Panel A). However, the nanovesicles with LP efficiently released the encapsulated carboxyfluorescein and that the dye was internalized in the spheroids (FIG. 8, Panel B).

Figure 9:
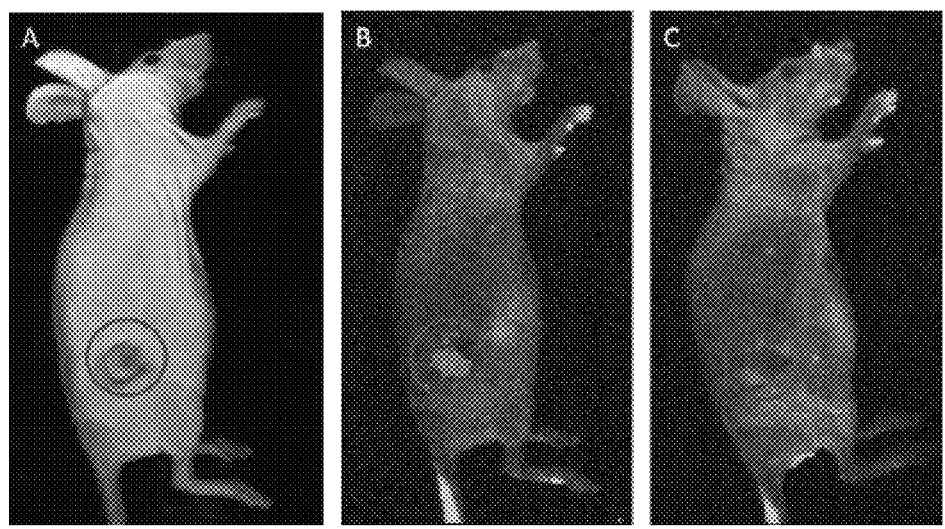
FIG. 9. Carboxyfluorescein release from nanovesicles was observed after 6 hours (B) and 24 hours (C) of injection via the tail vein in nude mice. Panel A represents a white-light image, and the circled areas indicate the tumor-bearing site.

The nanovesicles were observed to be stable in 10% human serum, suggesting stability in circulation before reaching the tumor site (FIG. 12). Live-animal imaging after 6 hours and 24 hours of tail-vain administration of carboxyfluorescein-encapsulated nanovesicles confirmed the stability and the effective release capability at the tumor site (FIG. 9).

Figure 10:
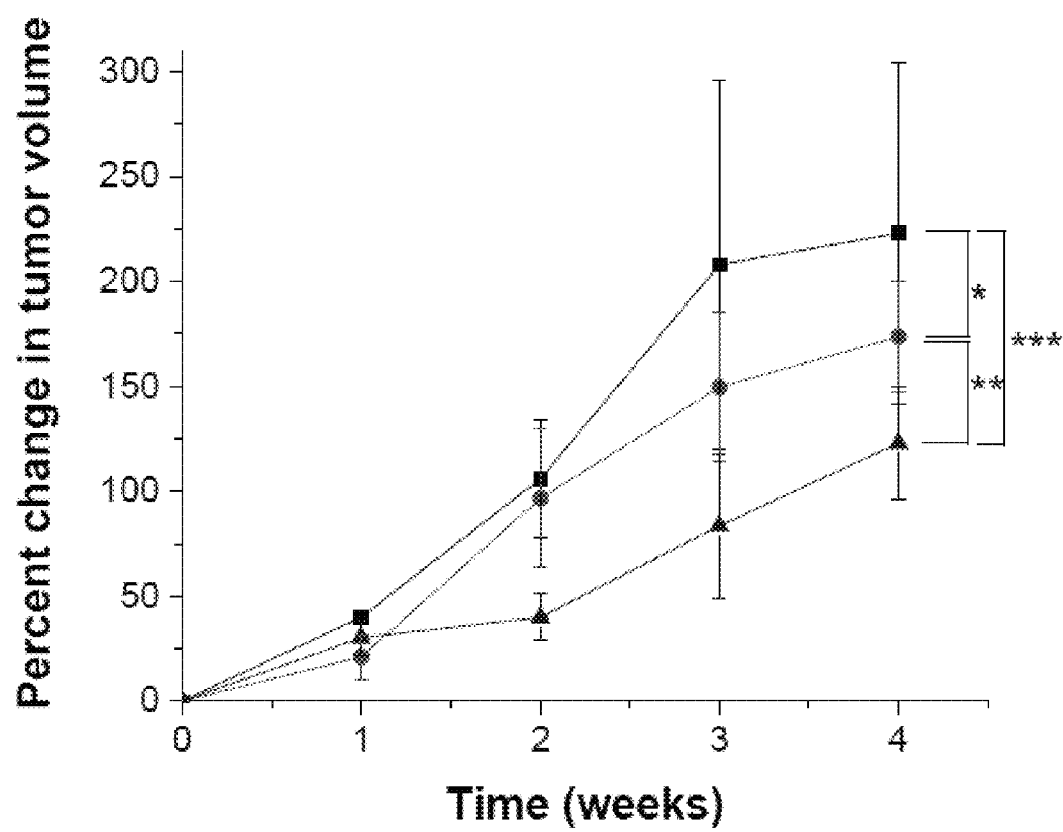
FIG. 10. The percentage increase in tumor volume for the test group (triangles, n=3) was lower in LP incorporated nanovesicle-treated mice as compared to the control (squares, n=3) and positive control treated mice (circles, n=3). (*p<0.05, p<0.05, *p<0.05).
Figure 13:
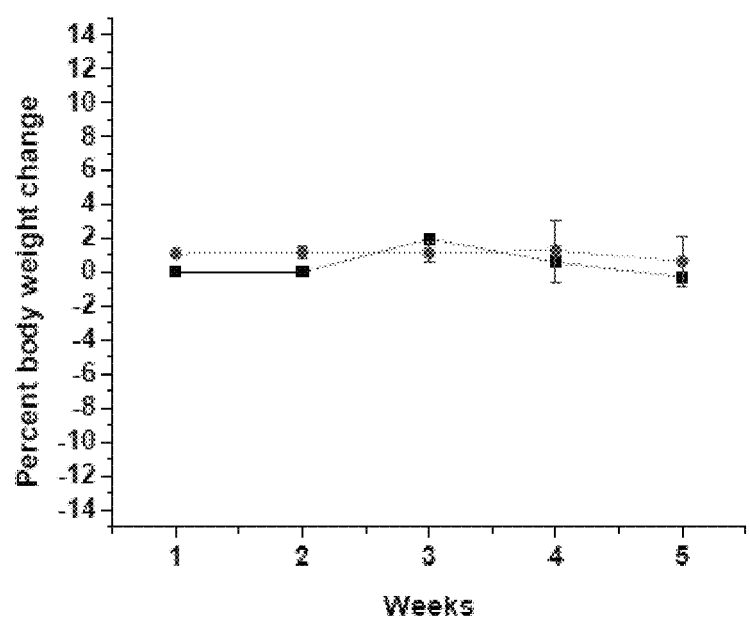
FIG. 13. Weight change in drug treated and control mice. Body weight changes for mice under study were monitored over 5 weeks during the treatment. Weight loss more than 15% was set as reference for toxicity. However, no significant weight loss was observed in control (squares) as well as gemcitabine nanovesicles treated group (circles).

Subsequently, the effectiveness of the proposed delivery strategy was demonstrated by employing a xenograft mouse model of human pancreatic cancer. For these studies, 9 athymic, female, Nude-Foxn1nu mice (5-6 weeks old) were used. The mice were divided in three groups (control, positive control and test), and were injected with 3 million PANC-1 cells subcutaneously. Tumors developed in the animals, 15 days after subcutaneous injections. The control group received the weekly injections (via the tail vain) of buffer while the animals in positive control and and test group received injections of gemcitabine-encapsulated nanovesicles (dose: 10 mg/kg/week) for 4 weeks. The animals from both the groups showed lesser tumor growth as compared to the control (FIG. 10). However, it was observed that the animals receiving gemcitabine encapsulated in PEGylated MMP-9 responsive nanovesicles showed more pronounced reduction in tumor growth (FIG. 10, triangles) as compared to animals receiving gemcitabine encapsulated in PEGylated liposomes without LP (FIG. 10, circles). Weight for all the animals receiving gemcitabine nanovesicles did not decrease during and after the treatment—indicating the lack of toxicity for the nanovesicle formulations (FIG. 13). After 4 weeks of treatment, the increased tumor volumes for the treated mice were substantially less compared to the control group (FIG. 10).

CONCLUSION

Described herein is the successful demonstration that the elevated levels of MMP-9 and GSH in the extracellular matrix of tumor tissues can be used to trigger contents release from suitably-constructed nanovesicles. These liposomes incorporate disulfide linked PEG groups on the surface. At the tumor site, elevated levels of glutathione reductively removes the PEG groups, exposing the MMP-9 substrate peptide towards enzymatic hydrolysis. The resultant destabilization of the lipid bilayer leads to rapid release of encapsulated contents. The anticancer drug gemcitabine was successfully encapsulated and demonstrated that the cytotoxicity of the released drug to pancreatic cancer cells (in monolayer and spheroid cultures) is comparable to that for the non-encapsulated drug. Internalization studies carried out using pancreatic cancer cell spheroids showed that the incorporated MMP-9-responsive lipopeptide triggers the drug release in the tumor's extracellular matrix. In-vivo imaging studies with the designed, long-circulating nanovesicles exhibited circulatory stability. In-vivo studies also confirmed the release of encapsulated gemcitabine in the tumor microenvironment, showing a reduction in tumor growth rate in nude mice. Better control was observed over tumor growth with the MMP-9 responsive nanovesicles compared to the PEGylated vesicles without the MMP-9 substrate lipopeptide.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A nanoparticle comprising a lipid layer and a compartment surrounded by the lipid layer,
wherein the lipid layer comprises (i) a first lipid, the first lipid comprising a POPE lipid covalently attached to a hydrophilic polymer by a disulfide bond, and (ii) a lipoprotein, the lipoprotein comprising a trigger protein,
wherein the concentration of the first lipid is between 1 mole percent (mol %) and 30 mol %, and
wherein the disulfide bond of the first lipid is stable under conditions comprising 10% human serum and is broken under conditions comprising 50 micromolar glutathione.

2. The nanoparticle of claim 1 wherein the trigger protein comprises an amino acid repeat region.

3. The nanoparticle of claim 2 wherein the amino acid repeat region comprises (GPX)n, wherein X is 4-hydroxyproline or proline, and n is at least 3.

4. The nanoparticle of claim 2 wherein the trigger protein comprises a peptide bond that is cleaved by a gelatinase or a member of the ADAM family of proteases.

5. The nanoparticle of claim 4 wherein the gelatinase is gelatinase-B protease.

6. The nanoparticle of claim 4 wherein the member of the ADAM family of proteases is ADAM10 protease.

7. The nanoparticle of claim 6 wherein the trigger protein comprises an amino acid sequence GPL GLA RKG (GPO)$_4$ (SEQ ID NO:15).

8. The nanoparticle of claim 1 wherein the compartment comprises a compound.

9. The nanoparticle of claim 8 wherein the compound is an inhibitor of a gelatinase or a member of the ADAM family of proteases.

10. The nanoparticle of claim 8 wherein the compound is a therapeutic agent.

11. The nanoparticle of claim 8 wherein the compound is a non-therapeutic agent.

12. A nanoparticle comprising a lipid layer and a compartment surrounded by the lipid layer,
wherein the lipid layer comprises (i) a first lipid, the first lipid covalently attached to a hydrophilic polymer by a disulfide bond, and (ii) a lipoprotein, the lipoprotein comprising a trigger protein, wherein the trigger protein comprises a peptide bond that is cleaved by a member of the ADAM family of proteases,
wherein the concentration of the first lipid is between 1 mole percent (mol %) and 30 mol %, and
wherein the disulfide bond of the first lipid is stable under conditions comprising 10% human serum and is broken under conditions comprising 50 micromolar glutathione.

13. The nanoparticle of claim 12 wherein the member of the ADAM family of proteases is ADAM10 protease.

14. The nanoparticle of claim 13 wherein the trigger protein comprises an amino acid sequence GPL GLA RKG (GPO)$_4$ (SEQ ID NO:15).

15. The nanoparticle of claim 12 wherein the compartment comprises a compound.

16. The nanoparticle of claim 15 wherein the compound is an inhibitor of a member of the ADAM family of proteases.

17. The nanoparticle of claim 15 wherein the compound is a therapeutic agent.

18. The nanoparticle of claim 15 wherein the compound is a non-therapeutic agent.

19. A method for delivering a compound to an environment, the method comprising:
providing the nanoparticle of claim 1, wherein the compartment comprises a compound;
exposing the nanoparticle to an environment comprising (i) a reducing agent at a concentration sufficient to break the disulfide bond of the first lipid, and (ii) an enzyme that cleaves a peptide bond of the trigger protein, wherein exposure of the nanoparticle to the environment results in release of the compound from the compartment.

* * * * *